(12) United States Patent
Kunz et al.

(10) Patent No.: US 9,051,519 B2
(45) Date of Patent: Jun. 9, 2015

(54) DIENE-SELECTIVE HYDROGENATION OF METATHESIS DERIVED OLEFINS AND UNSATURATED ESTERS

(71) Applicant: ELEVANCE RENEWABLE SCIENCES, INC., Woodridge, IL (US)

(72) Inventors: Linda A. Kunz, Naperville, IL (US); Tessa M. Pals, Chicago, IL (US); Steven A. Cohen, Naperville, IL (US); Melvin L. Luetkens, Jr., Batavia, IL (US); Chander Balakrishnan, Oak Park, IL (US); Robert B. Snyder, Naperville, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 217 days.

(21) Appl. No.: 13/827,153

(22) Filed: Mar. 14, 2013

(65) Prior Publication Data

US 2013/0217906 A1    Aug. 22, 2013

Related U.S. Application Data

(63) Continuation-in-part of application No. 13/647,825, filed on Oct. 9, 2012, now Pat. No. 8,735,640, and a continuation-in-part of application No. 12/901,829, filed on Oct. 11, 2010, now Pat. No. 8,957,268.

(60) Provisional application No. 61/250,743, filed on Oct. 12, 2009.

(51) Int. Cl.
    *C07C 1/00*    (2006.01)
    *C07C 6/02*    (2006.01)
    (Continued)

(52) U.S. Cl.
    CPC ... *C10G 3/50* (2013.01); *C11C 3/12* (2013.01); *C10G 3/44* (2013.01); *C10G 29/205* (2013.01);
    (Continued)

(58) Field of Classification Search
    USPC .................. 585/324, 240, 643, 271
    See application file for complete search history.

(56) References Cited

U.S. PATENT DOCUMENTS 2,190,593 A    2/1940    Clayton
2,484,841 A    10/1949   Lorand
(Continued)

FOREIGN PATENT DOCUMENTS

EP    0 116 408 A2    8/1984
EP    0 429 995 A2    6/1991
(Continued)

OTHER PUBLICATIONS

Ackman, R.G. et al., "Ozonolysis of Unsaturated Fatty Acids," *Can. J. Chem.*, vol. 39, 1961, pp. 1956-1963.
(Continued)

*Primary Examiner* — Thuan D Dang
(74) *Attorney, Agent, or Firm* — Robert S. Dailey

(57) ABSTRACT

Methods are provided for refining natural oil feedstocks and partially hydrogenating polyunsaturated olefins and polyunsaturated esters. The methods comprise reacting the feedstock in the presence of a metathesis catalyst under conditions sufficient to form a metathesized product comprising olefins and esters. In certain embodiments, the methods further comprise separating the polyunsaturated olefins from the polyunsaturated esters in the metathesized product. In certain embodiments, the methods further comprise partially hydrogenating the polyunsaturated olefins in the presence of a hydrogenation catalyst, wherein at least a portion of the polyunsaturated olefins are converted to monounsaturated olefins. In other embodiments, the methods further comprise partially hydrogenating the polyunsaturated esters in the presence of a hydrogenation catalyst, wherein at least a portion of the polyunsaturated esters are converted to monounsaturated esters.

21 Claims, 1 Drawing Sheet

(51) Int. Cl.
*C07C 5/05* (2006.01)
*C10G 3/00* (2006.01)
*C11C 3/12* (2006.01)
*C10G 29/20* (2006.01)
*C10G 45/00* (2006.01)
*C10G 45/58* (2006.01)
*C10G 50/00* (2006.01)
*C10G 65/04* (2006.01)
*C10G 69/12* (2006.01)
*C11B 3/00* (2006.01)
*C10L 1/02* (2006.01)
*C10L 1/08* (2006.01)
*C11C 3/00* (2006.01)
*C11C 3/10* (2006.01)
*C07C 6/04* (2006.01)
*C07C 1/213* (2006.01)
*C07C 5/03* (2006.01)
*C07C 7/13* (2006.01)

(52) U.S. Cl.
CPC ............... *C10G 45/00* (2013.01); *C10G 45/58* (2013.01); *C10G 50/00* (2013.01); *C10G 65/043* (2013.01); *C10G 69/123* (2013.01); *C11B 3/00* (2013.01); *C10L 1/026* (2013.01); *C10L 1/08* (2013.01); *C11C 3/003* (2013.01); *C11C 3/10* (2013.01); *C10G 3/42* (2013.01); C10G 2300/1014 (2013.01); C10G 2300/1018 (2013.01); C10G 2300/1088 (2013.01); C10G 2300/30 (2013.01); C10G 2400/02 (2013.01); C10G 2400/04 (2013.01); C10G 2400/08 (2013.01); C10G 2400/20 (2013.01); C10G 2400/22 (2013.01); *C07C 6/04* (2013.01); *C07C 5/05* (2013.01); C07C 2523/72 (2013.01); C07C 2523/755 (2013.01); *C07C 1/213* (2013.01); *C07C 5/03* (2013.01); *C07C 7/13* (2013.01); C07C 2523/28 (2013.01); C07C 2523/42 (2013.01); C07C 2523/44 (2013.01); C07C 2523/46 (2013.01); C07C 2523/745 (2013.01); C10L 2200/0469 (2013.01); C10L 2200/0476 (2013.01)

(56) References Cited

U.S. PATENT DOCUMENTS

| | | |
|---|---|---|
| 3,150,205 A | 9/1964 | Krane et al. |
| 3,351,566 A | 11/1967 | Taylor et al. |
| 3,507,890 A | 4/1970 | Dieckmann et al. |
| 3,896,053 A | 7/1975 | Broecker et al. |
| 4,210,771 A | 7/1980 | Holcombe |
| 4,465,890 A | 8/1984 | Kukes et al. |
| 4,554,065 A | 11/1985 | Albinson et al. |
| 4,943,396 A | 7/1990 | Johnson |
| 4,992,605 A | 2/1991 | Craig et al. |
| 5,043,485 A | 8/1991 | Fleckenstein et al. |
| 5,091,116 A | 2/1992 | Krishnamurthy et al. |
| 5,095,169 A | 3/1992 | Skeels et al. |
| 5,113,030 A | 5/1992 | Chen et al. |
| 5,120,896 A | 6/1992 | Kemp et al. |
| 5,142,072 A | 8/1992 | Stipp et al. |
| 5,146,033 A | 9/1992 | Schrock et al. |
| 5,191,145 A | 3/1993 | Allen et al. |
| 5,262,076 A | 11/1993 | Ishida et al. |
| 5,264,606 A | 11/1993 | Moloy et al. |
| 5,298,271 A | 3/1994 | Takashina et al. |
| 5,298,638 A | 3/1994 | Toeneboehn et al. |
| 5,342,909 A | 8/1994 | Grubbs et al. |
| 5,348,755 A | 9/1994 | Roy |
| 5,374,751 A | 12/1994 | Cheng et al. |
| 5,391,385 A | 2/1995 | Seybold |
| 5,399,731 A | 3/1995 | Wimmer |
| 5,401,866 A | 3/1995 | Cheng et al. |
| 5,414,184 A | 5/1995 | Wu et al. |
| 5,432,083 A | 7/1995 | Copeland et al. |
| 5,484,201 A | 1/1996 | Goolsbee |
| 5,532,163 A | 7/1996 | Yagi et al. |
| 5,560,950 A | 10/1996 | Conte et al. |
| 5,596,111 A | 1/1997 | Sibi et al. |
| 5,597,600 A | 1/1997 | Munson et al. |
| 5,653,966 A | 8/1997 | Bertoli et al. |
| 5,672,802 A | 9/1997 | Lutz |
| 5,675,051 A | 10/1997 | Chauvin et al. |
| 5,734,070 A | 3/1998 | Tacke et al. |
| 5,747,409 A | 5/1998 | Commereuc |
| 5,824,354 A | 10/1998 | Ritter et al. |
| 5,840,942 A | 11/1998 | Oude Alink |
| 5,864,049 A | 1/1999 | Dos Santos et al. |
| 5,880,298 A | 3/1999 | Hillion et al. |
| 5,883,272 A | 3/1999 | Noweck et al. |
| 5,932,261 A | 8/1999 | Unnithan |
| 5,939,572 A | 8/1999 | Sibi et al. |
| 5,959,129 A | 9/1999 | van Dam et al. |
| 5,972,057 A | 10/1999 | Hayafuji et al. |
| 6,033,706 A | 3/2000 | Silkeberg et al. |
| 6,075,158 A | 6/2000 | Hill |
| 6,127,560 A | 10/2000 | Stidham et al. |
| 6,127,561 A | 10/2000 | Jeromin et al. |
| 6,129,945 A | 10/2000 | Awad et al. |
| 6,162,480 A | 12/2000 | van Buuren et al. |
| 6,166,279 A | 12/2000 | Schwab et al. |
| 6,172,248 B1 | 1/2001 | Copeland et al. |
| 6,175,047 B1 | 1/2001 | Hori et al. |
| 6,197,894 B1 | 3/2001 | Sunaga et al. |
| 6,207,209 B1 | 3/2001 | Jirjis et al. |
| 6,210,732 B1 | 4/2001 | Papanton |
| 6,211,315 B1 | 4/2001 | Larock et al. |
| 6,214,764 B1 | 4/2001 | Gillespie |
| 6,215,019 B1 | 4/2001 | Pederson et al. |
| 6,248,911 B1 | 6/2001 | Canessa et al. |
| 6,251,460 B1 | 6/2001 | Ganguli et al. |
| 6,265,495 B1 | 7/2001 | Hirata et al. |
| 6,271,430 B2 | 8/2001 | Schwab et al. |
| 6,281,163 B1 | 8/2001 | Van Dijk |
| 6,284,852 B1 | 9/2001 | Lynn et al. |
| 6,288,251 B1 | 9/2001 | Tsuto et al. |
| 6,303,837 B1 | 10/2001 | Gürtler et al. |
| 6,313,365 B1 | 11/2001 | Hori et al. |
| 6,368,648 B1 | 4/2002 | Bertram et al. |
| 6,376,581 B1 | 4/2002 | Tanaka et al. |
| 6,388,038 B1 | 5/2002 | Hirata et al. |
| 6,395,669 B1 | 5/2002 | Sartain et al. |
| 6,409,778 B1 | 6/2002 | Auschra et al. |
| 6,440,057 B1 | 8/2002 | Ergün et al. |
| 6,486,264 B1 | 11/2002 | Tsunogae et al. |
| 6,492,564 B1 | 12/2002 | Wiese et al. |
| 6,506,944 B1 | 1/2003 | Schwab et al. |
| 6,552,139 B1 | 4/2003 | Herrmann et al. |
| 6,552,208 B1 | 4/2003 | Alander et al. |
| 6,583,236 B1 | 6/2003 | Giardello et al. |
| 6,605,748 B2 | 8/2003 | Wagener et al. |
| 6,638,551 B1 | 10/2003 | Levy et al. |
| 6,646,172 B1 | 11/2003 | Schwab et al. |
| 6,677,495 B1 | 1/2004 | Schwab et al. |
| 6,696,597 B2 | 2/2004 | Pedersen et al. |
| 6,706,299 B2 | 3/2004 | Thengumpillil et al. |
| 6,716,155 B2 | 4/2004 | Sleeter |
| 6,740,134 B2 | 5/2004 | Angelico et al. |
| 6,758,869 B2 | 7/2004 | Roeske et al. |
| 6,761,869 B1 | 7/2004 | Virtanen |
| 6,800,316 B1 | 10/2004 | Perrut et al. |
| 6,833,149 B2 | 12/2004 | Jirjis et al. |
| 6,846,772 B2 | 1/2005 | Lok et al. |
| 6,852,900 B2 | 2/2005 | Wurziger et al. |
| 6,900,347 B2 | 5/2005 | Paulson et al. |
| 6,916,448 B2 | 7/2005 | Commereuc et al. |
| 6,960,272 B1 | 11/2005 | Tokas et al. |
| 6,962,729 B2 | 11/2005 | Tokas et al. |
| 6,982,155 B1 | 1/2006 | Fukuda et al. |
| 6,987,154 B2 | 1/2006 | Choi et al. |

(56) References Cited

U.S. PATENT DOCUMENTS

| | | |
|---|---|---|
| 6,998,050 B2 | 2/2006 | Nakajoh et al. |
| 7,025,851 B2 | 4/2006 | Caster et al. |
| 7,026,495 B1 | 4/2006 | Pedersen et al. |
| 7,045,100 B2 | 5/2006 | Ergün et al. |
| 7,045,114 B2 | 5/2006 | Tonkovich et al. |
| 7,060,316 B2 | 6/2006 | Sakai et al. |
| 7,067,584 B2 | 6/2006 | Rink et al. |
| 7,119,216 B2 | 10/2006 | Newman et al. |
| 7,141,083 B2 | 11/2006 | Jordan |
| 7,144,433 B2 | 12/2006 | Jordan |
| 7,144,435 B2 | 12/2006 | Jordan |
| 7,160,338 B2 | 1/2007 | Jordan |
| 7,160,339 B2 | 1/2007 | Jordan |
| 7,176,336 B2 | 2/2007 | Maughon et al. |
| 7,220,289 B2 | 5/2007 | Jordan |
| 7,276,616 B2 | 10/2007 | Dwyer et al. |
| 7,314,904 B2 | 1/2008 | Nadolsky et al. |
| 7,320,809 B2 | 1/2008 | Friedman et al. |
| 7,361,621 B2 | 4/2008 | Yang et al. |
| 7,365,140 B2 | 4/2008 | Piers et al. |
| 7,431,749 B2 | 10/2008 | Kim et al. |
| 7,442,248 B2 | 10/2008 | Timmons |
| 7,449,591 B2 | 11/2008 | Brenner et al. |
| 7,452,515 B1 | 11/2008 | Lafleur et al. |
| 7,507,846 B2 | 3/2009 | Pelly |
| 7,507,854 B2 | 3/2009 | Lee et al. |
| 7,511,101 B2 | 3/2009 | Nguyen et al. |
| 7,553,982 B1 | 6/2009 | Morris |
| 7,563,915 B2 | 7/2009 | Matson et al. |
| 7,576,227 B2 | 8/2009 | Lysenko et al. |
| 7,585,990 B2 | 9/2009 | van Toor et al. |
| 7,597,783 B2 | 10/2009 | Kruidenberg |
| 7,598,407 B2 | 10/2009 | Kruidenberg |
| 7,601,309 B2 | 10/2009 | Krupa et al. |
| 7,612,221 B2 | 11/2009 | Haas et al. |
| 7,626,047 B2 | 12/2009 | Nakayama et al. |
| 7,626,048 B2 | 12/2009 | Soane et al. |
| 7,645,807 B1 | 1/2010 | Goetsch et al. |
| 7,652,145 B2 | 1/2010 | Herrmann et al. |
| 7,652,156 B2 | 1/2010 | Hillion et al. |
| 7,666,234 B2 | 2/2010 | Ghosh et al. |
| 7,671,224 B2 | 3/2010 | Winde et al. |
| 7,678,932 B2 | 3/2010 | Thurier et al. |
| 7,695,533 B2 | 4/2010 | Kovacs et al. |
| 7,696,376 B2 | 4/2010 | Furuta |
| 7,696,398 B2 | 4/2010 | Burdett et al. |
| 7,718,833 B2 | 5/2010 | Potthast et al. |
| 7,737,233 B2 | 6/2010 | Obrecht et al. |
| 7,743,828 B2 | 6/2010 | Roddy et al. |
| 7,745,652 B2 | 6/2010 | Lysenko et al. |
| 7,750,172 B2 | 7/2010 | Grubbs et al. |
| 7,790,651 B2 | 9/2010 | Lin et al. |
| 7,806,945 B2 | 10/2010 | Jackam et al. |
| 7,812,185 B2 | 10/2010 | Burdett et al. |
| 7,812,187 B2 | 10/2010 | Kawashima et al. |
| 7,838,711 B2 | 11/2010 | Herweck et al. |
| 7,846,995 B2 | 12/2010 | Ong et al. |
| 7,858,710 B2 | 12/2010 | Wagener et al. |
| 7,863,471 B2 | 1/2011 | Krause et al. |
| 7,875,736 B2 | 1/2011 | Wang et al. |
| 7,902,417 B2 | 3/2011 | Goldman et al. |
| 7,905,288 B2 | 3/2011 | Kinkead |
| 7,906,665 B2 | 3/2011 | Lin et al. |
| 7,939,688 B2 | 5/2011 | Meudt et al. |
| 7,951,967 B2 | 5/2011 | Chun et al. |
| 7,960,598 B2 | 6/2011 | Spilker et al. |
| 8,039,652 B2 | 10/2011 | Portnoff et al. |
| 8,039,653 B2 | 10/2011 | Soane et al. |
| 8,044,149 B2 | 10/2011 | Iwasaki et al. |
| 8,066,954 B2 | 11/2011 | Nguyen et al. |
| 8,071,799 B2 | 12/2011 | Olson |
| 8,147,766 B2 | 4/2012 | Spilker et al. |
| 8,148,477 B2 | 4/2012 | Saita et al. |
| 8,163,946 B2 | 4/2012 | Yan et al. |
| 8,192,696 B2 | 6/2012 | Gurski et al. |
| 8,207,362 B2 | 6/2012 | Morris |
| 8,227,371 B2 | 7/2012 | Holtcamp et al. |
| 8,227,635 B2 | 7/2012 | Bowden et al. |
| 8,237,003 B2 | 8/2012 | Holtcamp et al. |
| 8,293,181 B2 | 10/2012 | Saita et al. |
| 8,309,055 B2 | 11/2012 | Arstad et al. |
| 8,324,334 B2 | 12/2012 | Jones et al. |
| 8,324,413 B2 | 12/2012 | O'Rear |
| 8,334,396 B2 | 12/2012 | Papadogianakis et al. |
| 2002/0095007 A1 | 7/2002 | Larock et al. |
| 2003/0055184 A1 | 3/2003 | Song et al. |
| 2003/0135080 A1 | 7/2003 | Botha et al. |
| 2003/0236175 A1 | 12/2003 | Twu et al. |
| 2005/0027136 A1 | 2/2005 | Toor et al. |
| 2005/0070750 A1 | 3/2005 | Newman et al. |
| 2005/0080301 A1 | 4/2005 | Maughon et al. |
| 2005/0154221 A1 | 7/2005 | Lysenko et al. |
| 2005/0203324 A1 | 9/2005 | Lee et al. |
| 2006/0042158 A1 | 3/2006 | Lee |
| 2006/0047176 A1 | 3/2006 | Gartside et al. |
| 2006/0069274 A1 | 3/2006 | Dias De Moraes E. Silva et al. |
| 2006/0079704 A1 | 4/2006 | Lacombe et al. |
| 2006/0167326 A1 | 7/2006 | Burdett et al. |
| 2006/0289138 A1 | 12/2006 | Borsinger et al. |
| 2007/0011943 A1 | 1/2007 | Lin |
| 2007/0151146 A1 | 7/2007 | Lee et al. |
| 2007/0179302 A1 | 8/2007 | Olivier-Bourbigou et al. |
| 2007/0179307 A1 | 8/2007 | Olivier-Bourbigou et al. |
| 2007/0208206 A1 | 9/2007 | Obrecht et al. |
| 2007/0217965 A1 | 9/2007 | Johnson et al. |
| 2007/0225536 A1 | 9/2007 | Lutz |
| 2007/0227400 A1 | 10/2007 | Zullo et al. |
| 2007/0270621 A1 | 11/2007 | Millis et al. |
| 2007/0277430 A1 | 12/2007 | Jackman et al. |
| 2008/0027194 A1 | 1/2008 | Schrodi |
| 2008/0047194 A1 | 2/2008 | Prawoto |
| 2008/0064891 A1 | 3/2008 | Lee |
| 2008/0097114 A1 | 4/2008 | Bakshi |
| 2008/0103346 A1 | 5/2008 | Burdett et al. |
| 2008/0115407 A1 | 5/2008 | Hoffman |
| 2008/0119664 A1 | 5/2008 | Sinoncelli et al. |
| 2008/0202021 A1 | 8/2008 | Powell |
| 2008/0228017 A1 | 9/2008 | Burdett et al. |
| 2008/0229654 A1 | 9/2008 | Bradin |
| 2008/0244962 A1 | 10/2008 | Abhari et al. |
| 2008/0282606 A1 | 11/2008 | Plaza et al. |
| 2008/0300434 A1 | 12/2008 | Cortright et al. |
| 2008/0306230 A1 | 12/2008 | Pan et al. |
| 2009/0038209 A1 | 2/2009 | Farid et al. |
| 2009/0048459 A1 | 2/2009 | Tupy et al. |
| 2009/0069516 A1 | 3/2009 | Obrecht et al. |
| 2009/0112007 A1 | 4/2009 | Lin et al. |
| 2009/0126602 A1 | 5/2009 | Murphy et al. |
| 2009/0143544 A1 | 6/2009 | Lysenko et al. |
| 2009/0145022 A1 | 6/2009 | Ng et al. |
| 2009/0163731 A1 | 6/2009 | Martin et al. |
| 2009/0165366 A1 | 7/2009 | Jovanovic et al. |
| 2009/0178330 A1 | 7/2009 | Lebron Parejo et al. |
| 2009/0183420 A1 | 7/2009 | Cobb |
| 2009/0203860 A1 | 8/2009 | Bergbreiter et al. |
| 2009/0217568 A1 | 9/2009 | Murphy et al. |
| 2009/0220443 A1 | 9/2009 | Braksmayer et al. |
| 2009/0259065 A1 | 10/2009 | Abraham et al. |
| 2009/0264672 A1 | 10/2009 | Abraham et al. |
| 2009/0287004 A1 | 11/2009 | Bergman et al. |
| 2009/0306441 A1 | 12/2009 | Basset et al. |
| 2009/0307966 A1 | 12/2009 | Yan et al. |
| 2009/0324514 A1 | 12/2009 | Awad |
| 2009/0326295 A1 | 12/2009 | Krupa et al. |
| 2010/0010246 A1 | 1/2010 | Yan et al. |
| 2010/0018902 A1 | 1/2010 | Brownscombe et al. |
| 2010/0022789 A1 | 1/2010 | Mignani et al. |
| 2010/0037667 A1 | 2/2010 | Calderon et al. |
| 2010/0043280 A1 | 2/2010 | Morris |
| 2010/0047499 A1 | 2/2010 | Braksmayer et al. |
| 2010/0087671 A1 | 4/2010 | Lemke |
| 2010/0093944 A1 | 4/2010 | Müller et al. |
| 2010/0094034 A1 | 4/2010 | Kaido et al. |
| 2010/0107474 A1 | 5/2010 | Talwar et al. |

(56) References Cited

U.S. PATENT DOCUMENTS

| | | |
|---|---|---|
| 2010/0113719 A1 | 5/2010 | Patton et al. |
| 2010/0121087 A1 | 5/2010 | Banavali et al. |
| 2010/0130769 A1 | 5/2010 | Banavali et al. |
| 2010/0132252 A1 | 6/2010 | Nakazono |
| 2010/0140136 A1 | 6/2010 | Spilker et al. |
| 2010/0145086 A1 | 6/2010 | Schrodi et al. |
| 2010/0160506 A1 | 6/2010 | Wu et al. |
| 2010/0163459 A1 | 7/2010 | Odueyungbo |
| 2010/0166620 A1 | 7/2010 | Gurski et al. |
| 2010/0167910 A1 | 7/2010 | Odueyungbo |
| 2010/0191008 A1 | 7/2010 | Olson |
| 2010/0212219 A1 | 8/2010 | Siochi et al. |
| 2010/0212220 A1 | 8/2010 | Tirmizi |
| 2010/0223842 A1 | 9/2010 | Thesz et al. |
| 2010/0228042 A1 | 9/2010 | Chun et al. |
| 2010/0234625 A1 | 9/2010 | Papadogianakis et al. |
| 2010/0236984 A1 | 9/2010 | Brookhart et al. |
| 2010/0242348 A1 | 9/2010 | Chen et al. |
| 2010/0243961 A1 | 9/2010 | Hilton et al. |
| 2010/0252485 A1 | 10/2010 | Soane et al. |
| 2010/0263263 A1 | 10/2010 | O'Rear |
| 2010/0264015 A1 | 10/2010 | Portnoff et al. |
| 2010/0282467 A1 | 11/2010 | Hutchison et al. |
| 2010/0307051 A1 | 12/2010 | Tremblay et al. |
| 2010/0312012 A1 | 12/2010 | Hannen et al. |
| 2010/0331558 A1 | 12/2010 | Kao et al. |
| 2011/0015419 A1 | 1/2011 | Pendleton et al. |
| 2011/0015434 A1 | 1/2011 | Hannen et al. |
| 2011/0077360 A1 | 3/2011 | Obrecht et al. |
| 2011/0087056 A1 | 4/2011 | Tirtowidjojo et al. |
| 2011/0113679 A1 | 5/2011 | Cohen et al. |
| 2011/0160472 A1 | 6/2011 | Lemke et al. |
| 2011/0190524 A1 | 8/2011 | Winde et al. |
| 2011/0198535 A1 | 8/2011 | Meier et al. |
| 2011/0237850 A1 | 9/2011 | Luetkens, Jr. et al. |
| 2011/0252696 A1 | 10/2011 | Franklin et al. |
| 2011/0313180 A1 | 12/2011 | Uptain et al. |
| 2012/0009133 A1 | 1/2012 | Leonard et al. |
| 2012/0035392 A1 | 2/2012 | Kobayashi et al. |
| 2012/0077235 A1 | 3/2012 | Olson |
| 2012/0088943 A1 | 4/2012 | Knuuttila et al. |
| 2012/0116138 A1 | 5/2012 | Goodall et al. |
| 2012/0152723 A1 | 6/2012 | Yoneya |
| 2012/0165293 A1 | 6/2012 | Yiannikouros et al. |
| 2012/0165589 A1 | 6/2012 | Partington |
| 2012/0171090 A1 | 7/2012 | Chang |
| 2012/0178913 A1 | 7/2012 | Lin et al. |
| 2012/0190806 A1 | 7/2012 | Jakel et al. |
| 2012/0197031 A1 | 8/2012 | Firth et al. |
| 2012/0197032 A1 | 8/2012 | Firth et al. |
| 2012/0271019 A1 | 10/2012 | Drozdzak |
| 2012/0289729 A1 | 11/2012 | Holtcamp et al. |
| 2012/0329941 A1 | 12/2012 | Ong et al. |

FOREIGN PATENT DOCUMENTS

| | | |
|---|---|---|
| EP | 0 167 201 B2 | 11/1995 |
| EP | 0 168 091 B2 | 4/2003 |
| EP | 1 408 064 A1 | 4/2004 |
| EP | 1 728 844 A1 | 12/2006 |
| EP | 1 810 960 A1 | 7/2007 |
| FR | 2 878 246 A1 | 5/2006 |
| JP | 56-077243 A | 6/1981 |
| JP | 05-004938 A | 1/1993 |
| JP | 09-014574 A | 1/1997 |
| SU | 1565872 A1 | 7/1988 |
| WO | WO 94/23836 A1 | 10/1994 |
| WO | WO 96/04289 A1 | 2/1996 |
| WO | WO 01/36368 A1 | 5/2001 |
| WO | WO 01/83097 A2 | 11/2001 |
| WO | WO 02/10114 A2 | 2/2002 |
| WO | WO 02/076920 A1 | 10/2002 |
| WO | WO 02/083742 A2 | 10/2002 |
| WO | WO 03/093215 A1 | 11/2003 |
| WO | WO 2004/062763 A2 | 7/2004 |
| WO | WO 2005/080455 A1 | 9/2005 |
| WO | WO 2006/043281 A1 | 4/2006 |
| WO | WO 2006/052688 A2 | 5/2006 |
| WO | WO 2006/076364 A2 | 7/2006 |
| WO | WO 2007/027669 A1 | 3/2007 |
| WO | WO 2007/027955 A2 | 3/2007 |
| WO | WO 2007/081987 A2 | 7/2007 |
| WO | WO 2007/092632 A2 | 8/2007 |
| WO | WO 2007/103398 A1 | 9/2007 |
| WO | WO 2007/103460 A2 | 9/2007 |
| WO | WO 2007/113530 A2 | 10/2007 |
| WO | WO 2008/008420 A1 | 1/2008 |
| WO | WO 2008/010961 A2 | 1/2008 |
| WO | WO 2008/046106 A2 | 4/2008 |
| WO | WO 2008/048520 A2 | 4/2008 |
| WO | WO 2008/048522 A1 | 4/2008 |
| WO | WO 2008/058664 A1 | 5/2008 |
| WO | WO 2008/063322 A2 | 5/2008 |
| WO | WO 2008/104929 A1 | 9/2008 |
| WO | WO 2008/140468 A2 | 11/2008 |
| WO | WO 2008/152371 A1 | 12/2008 |
| WO | WO 2009/007234 A1 | 1/2009 |
| WO | WO 2009/020665 A1 | 2/2009 |
| WO | WO 2009/020667 A1 | 2/2009 |
| WO | WO 2009/065229 A1 | 5/2009 |
| WO | WO 2009/089591 A1 | 7/2009 |
| WO | WO 2010/021740 A1 | 2/2010 |
| WO | WO 2010/051268 A1 | 5/2010 |
| WO | WO 2010/062958 A1 | 6/2010 |
| WO | WO 2010/074738 A1 | 7/2010 |
| WO | WO 2010/096549 A2 | 8/2010 |
| WO | WO 2010/097519 A2 | 9/2010 |
| WO | WO 2010/104844 A2 | 9/2010 |
| WO | WO 2010/124030 A1 | 10/2010 |
| WO | WO 2010/129051 A1 | 11/2010 |
| WO | WO 2011/046872 A2 | 4/2011 |
| WO | WO 2011/149789 A1 | 12/2011 |
| WO | WO 2012/004489 A1 | 1/2012 |

OTHER PUBLICATIONS

Ahn, Y.M. et al., "A Convenient Method for the Efficient Removal of Ruthenium Byproducts Generated during Olefin Metathesis Reactions," Org. Lett., 2001, vol. 3, pp. 1411-1413.

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis of Fatty Acid Esters," JAOCS, vol. 61(2), Feb. 1984, pp. 425-429.

Boelhouwer et al., "Metathesis Reactions of Fatty Acid Esters," Progress of Lipid Research, Pergamon Press, vol. 24, No. 3, 1985, pp. 243-267.

Bourgeois, Damien et al., "The $Cl_2(PCy3)(IMes)Ru(=CHPh)$ catalyst: olefin metathesis versus olefin isomerization," Journal of Organic Metallic Chemistry, vol. 643-644, 2002, pp. 247-252.

Bryan, Tom, "Adsorbing It All," *Biodiesel Magazine*, Mar. 2005, pp. 40-43.

Chatterjee et al., "Synthesis of Trisubstituted Alkenes via Olefin Cross-Metathesis," Organic Letters, vol. 1, No. 11, 1999, pp. 1751-1753.

Cho, J.H. et al., "An Efficient Method for Removal of Ruthenium Byproucts from Olefin Metathesis Reactions," Org. Lett., 2003, vol. 5, pp. 531-533.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

(56) References Cited

OTHER PUBLICATIONS

Cotton, F.A. et al., Advanced Inorganic Chemistry, Fifth Edition, New York, John Wiley & Sons, 1988, pp. 382-443.
Delaude et al., Metathesis, Kirk-Othmer Encyclopedia of Chemical Technology, Dec. 2005, vol. 26, pp. 920-958.
Dunne et al., "A Highly Efficient Olefin Metathesis Initiator: Improved Synthesis and Reactivity Studies," Tetrahedron Letters, vol. 44, No. 13, 2003, pp. 2733-2736.
Erhan et al., "Drying Properties of Metathesized Soybean Oil," Journal of American Oil Chemists' Society, AOCS Press, vol. 74, No. 6, 1997, pp. 703-706.
Foglia, T.A., et al., "Oxidation of Unsaturated Fatty Acids With Ruthenium and Osmium Tetroxide," *J. Am. Oil Chemists' Soc.*, vol. 54, Nov. 1977, pp. 870A-872A.
Formentin, P. et al., "Reactivity of Grubbs' Catalysts with Urea- and Amide-Substituted Olefins. Metathesis and Isomerization," J. Org. Chem., 2005, vol. 70, pp. 8235-8238.
Galan, B. R. et al., "A Rapid and Simple Cleanup Procedure for Metathesis Reactions," Org. Lett., 2007, vol. 9, pp. 1203-1206.
Gimeno, N. et al., "Phenylphosphoric Acid as a New Additive to Inhibit Olefin Isomerization in Ruthenium-Catalyzed Metathesis Reactions," Eur. J. Org. Chem., 2007, pp. 918-924.
Hong, S.H. et al., "Prevention of Undesirable Isomerization During Olefin Metathesis," J. Am. Chem. Soc., 2005, vol. 127, pp. 17160-17161.
James, B.R. et al., "Developments in the Chemistry of Tris(hydroxymehtyl)phosphine," Coordination Chemistry Reviews, 2010, vol. 254, pp. 420-430.
Knight, D.W. et al., "A Simple Oxidative Procedure for the Removal of Ruthenium Residues from Metathesis Reaction Products," Tetrahedron Letters, 2010, vol. 51, pp. 638-640.
Kram, Jerry W., "Cleaner and Clearer," *Biodiesel Magazine*, Jan. 2008, 4 pages.
Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.
Maynard et al., "Purification Technique for the Removal of Ruthenium from Olefin Metathesis Reaction Products," Tetrahedron Letters, vol. 40, No. 22, 1999, pp. 4137-4140.
McEleney, K. et al., "Functionalized Mesoporous Silicates for the Removal of Ruthenium from Reaction Mixtures," Org. Lett., 2006, vol. 8, pp. 2663-2666.
Mol, "Metathesis of unsaturated fatty acid esters and fatty oils," Journal of Molecualr Catalysis, vol. 90, 1994, pp. 185-199.
Mol et al., "Metathesis in Oleochemistry," J Braz Chem Soc, vol. 9, No. 1, 1998, pp. 1-11.
Mol, "Applications of Olefin Metathesis in Oleochemistry: An Example of Green Chemistry," Green Chemistry, Royal Society of Chemistry, Cambridge, GB, vol. 4, 2002, pp. 5-13.
Mol, "Catalytic Metathesis of Unsaturated Fatty Acid Esters and Oils," Topics in Catalysis, vol. 27, No. 1-4, 2004, pp. 97-104.
Ngo et al., Metathesis of Unsaturated Fatty Acids: Synthesis of Long-Chain Unsaturated-[alpha],[omega]-Dicarboxylic Acids, Journal of the American Oil Chemists, July 2006, vol. 83m Issue 7, p. 629, 9 pgs.
Noureddini, H. et al., "Liquid-Phase Catalytic Oxidation of Unsaturated Fatty Acids," *Journal of American Oil Chemists' Society*, vol. 76, No. 3, 1999, pp. 305-312.
Oakley, Michael A., "Practical Dihydroxylation and C-C Cleavage of Unsaturated Fatty Acids," *Journal of Molecular Catalysis A: Chemical*, vol. 150, 1999, pp. 105-111.
Othmer, Kirk, "Metathesis," Encyclopedia of Chemical Technology, vol. 26, Dec. 2005, pp. 920-958.
Paquette, L.A. et al., "A Convenient Method for Removing All Highly-Colored Byproducts Generated During Olefin Metathesis Reactions," Org. Lett., 2000, vol. 2, pp. 1259-1261.
Patel, Jim et al., "Cross-metathesis of unsaturated natural oils with 2-butene, High conversion and productive catalyst turnovers," Chem. Commun., 2005, pp. 5546-5547.
Patel, Jim et al., "High Conversion and Productive Catalyst Turnovers in Cross-Metathesis Reactions of Natural Oils With 2-Butene," *Green Chem.*, vol. 8, 2006, pp. 450-454.
Pederson, R.L. et al., "Applications of Olefin Cross Metathesis to Commercial Products," Advanced Synthesis & Cataysts, 2002, vol. 344, pp. 728-735.
Refvik et al., "Ruthenium-Catalyzed Metathesis of Vegetable Oils," Journal of American Oil Chemists' Society, AOCS Press, vol. 76, No. 1, 1999, pp. 93-98.
Refvik, M.D. et al., "The Chemistry of Metathesized Soybean Oil," JAOCS, vol. 76, No. 1, 1999, pp. 99-102.
Rüsch gen. Klaas, M., et al., "Transition-Metal Catalyzed Oxidative Cleavage of Unsaturated Fatty Acids," *Fat Sci. Technol.*, vol. 95(10), 1995, pp. 359-367.
Sakamuri, Raj, "Ester," Kirk-Othmer Encyclopedia of Chemical Technology, John Wiley & Sons, 2001, available online Dec. 19, 2003, 31 pages.
Santacesaria, E., et al., "Oxidative Cleavage of the Double Bond of Monoenic Fatty Chains in Two Steps: A New Promising Route to Azelaic Acid and Other Industrial Products," *Ind. Eng. Chem. Res.*, vol. 39, 2000, pp. 2766-2771.
Santacesaria, E. et al., "Double Bond Oxidative Cleavage of Monoenic Fatty Chains," *Catalysis Today*, vol. 79-80, 2003, pp. 59-65.
Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.
Seador, J.D. et al., "Distillation," Perry's Chemical Engineers Handbook, R.H. Perry and D.W. Green, eds., McGraw-Hill, 7th Ed., 1997, available online Mar. 1, 2001, 7 pages.
Throckmorton, P.E. et al., "Pilot Run, Plant Design and Cost Analysis for Reductive Ozonolysis of Methyl Soyate," *Research and Development Laboratories*, 1967, p. 643.
Tian et al., "Model Studies and the ADMET Polymerization of Soybean Oil," Journal of American Oil Chemists' Society, AOCS Press, vol. 79, No. 5, 2002, pp. 479-488.
Turnwald, S.E., et al., "Oleic Acid Oxidation Using Hydrogen Peroxide in Conjunction With Transition Metal Catalysis," *Journal of Materials Science Letters*, vol. 17, 1998, pp. 1305-1307.
Wang, H. et al., "Development of a Robust Ring-Closing Metathesis Reaction in the Synthesis of SB-462795, a Cathepsin K Inhibitor," Organic Process Research & Development, 2008, vol. 12, pp. 226-234.
International Search Report and Written Opinion of the International Searching Authority for International Application No. PCT/US2010/052174, dated Apr. 15, 2011, 9 pages.

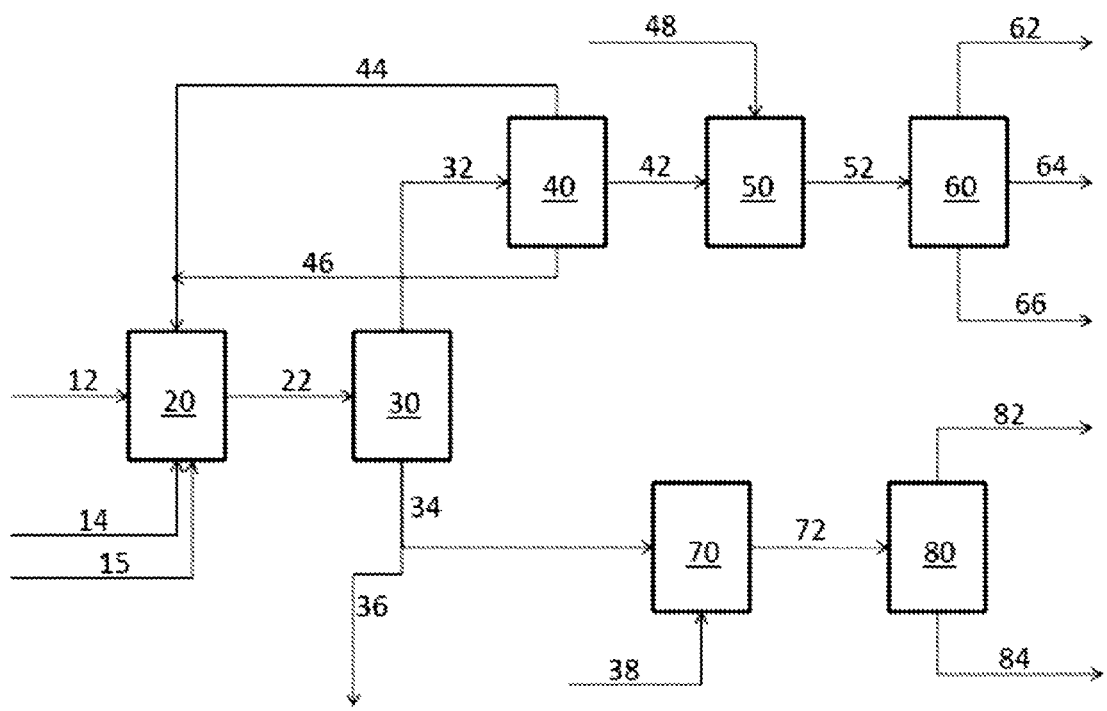

DIENE-SELECTIVE HYDROGENATION OF METATHESIS DERIVED OLEFINS AND UNSATURATED ESTERS

CROSS REFERENCE TO RELATED APPLICATIONS

This application is a continuation-in-part application of U.S. patent application Ser. No. 13/647,825, filed Oct. 9, 2012, and U.S. patent application Ser. No. 12/901,829, filed Oct. 11, 2010, which claims the benefit of U.S. Provisional Patent Application No. 61/250,743, filed Oct. 12, 2009, the disclosures of which are incorporated herein by reference.

BACKGROUND

Metathesis is a catalytic reaction generally known in the art that involves the interchange of alkylidene units among compounds containing one or more double bonds (e.g., olefinic compounds) via the formation and cleavage of the carbon-carbon double bonds. Metathesis may occur between two like molecules (often referred to as self-metathesis) and/or it may occur between two different molecules (often referred to as cross-metathesis). Self-metathesis may be represented schematically as shown in Equation I.

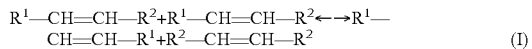
(I)

wherein $R^1$ and $R^2$ are organic groups.

Cross-metathesis may be represented schematically as shown in Equation II.

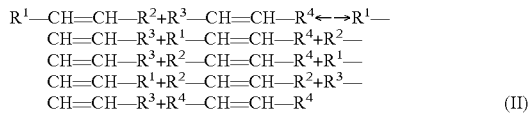
(II)

wherein $R^1$, $R^2$, $R^3$, and $R^4$ are organic groups.

In recent years, there has been an increased demand for environmentally friendly techniques for manufacturing materials typically derived from petroleum sources. For example, researchers have been studying the feasibility of manufacturing biofuels, waxes, plastics, and the like, using natural oil feedstocks, such as vegetable and seed-based oils. In one non-limiting example, metathesis catalysts are used to manufacture candle wax, as described in PCT/US2006/000822, which is herein incorporated by reference in its entirety. Metathesis reactions involving natural oil feedstocks offer promising solutions for today and for the future.

Natural oil feedstocks of interest include non-limiting examples such as natural oils (e.g., vegetable oils, fish oil, animal fats) and derivatives of natural oils, such as fatty acids and fatty acid alkyl (e.g., methyl) esters. These feedstocks may be converted into industrially useful chemicals (e.g., waxes, plastics, cosmetics, biofuels, etc.) by any number of different metathesis reactions. Significant reaction classes include, as non-limiting examples, self-metathesis, cross-metathesis with olefins, and ring-opening metathesis reactions. Representative non-limiting examples of useful metathesis catalysts are provided below. Metathesis catalysts can be expensive and, therefore, it is desirable to improve the efficiency of the metathesis catalyst.

In recent years, there has been an increased demand for petroleum-based transportation fuels. Concerns exist that the world's petroleum production may not be able to keep up with demand. Additionally, the increased demand for petroleum-based fuels has resulted in a higher production of greenhouse gases. In particular, the airline industry accounts for greater than 10% of the greenhouse gases within the United States. Due to the increased demand for fuel and increased production of greenhouse gases, there is a need to explore methods of producing environmentally-friendly, alternative fuel sources. In particular, there is a need to explore methods of producing environmentally friendly fuel compositions and specialty chemicals from a natural feedstock, including monounsaturated olefin compounds.

SUMMARY

Methods are disclosed for refining monounsaturated olefin compounds from a natural oil feedstock through a metathesis reaction of the natural oil feedstock in the presence of a metathesis catalyst.

In one embodiment, the method comprises providing a feedstock comprising a natural oil and reacting the feedstock in a metathesis reactor in the presence of a metathesis catalyst to form a metathesized product comprising polyunsaturated olefins and polyunsaturated esters. The method further comprises partially hydrogenating the polyunsaturated olefins and/or the polyunsaturated esters in the presence of a hydrogenation catalyst, wherein at least a portion of the polyunsaturated olefins and/or polyunsaturated esters are converted into monounsaturated olefins and/or monounsaturated esters. In some embodiments, the method further comprises separating the polyunsaturated olefins in the metathesized product from the polyunsaturated esters in the metathesized product prior to the hydrogenating step. In other embodiments, following the separating step and prior to the hydrogenating step, the method comprises transesterifying the polyunsaturated esters in the presence of an alcohol to form a transesterified product. In other alternative embodiments, following the separating step and the hydrogenating step, transesterifying the monounsaturated esters in the presence of an alcohol to form a transesterified product.

In some embodiments, at least a portion of the polyunsaturated olefins are converted into the monounsaturated olefins, and the conversion rate may be at least 85%, 90%, or 95%; and the selectivity may be at least 90%, 95%, or 99%. In other embodiments, at least a portion of the polyunsaturated esters are converted into the monounsaturated esters, and the conversion rate may be at least 85%, 90%, or 95%; and the selectivity may be at least 90%, 95%, or 99%. In certain embodiments, at least a portion of the polyunsaturated olefins are converted to the monounsaturated olefins and at least a portion of the polyunsaturated esters are converted to monounsaturated esters.

In some embodiments, the hydrogenation catalyst comprises a metal selected from the group consisting of nickel, copper, palladium, platinum, molybdenum, iron, ruthenium, osmium, rhodium, iridium, and combinations thereof. The hydrogenation catalyst may be provided in an amount between 0.01-1.0 wt % of the polyunsaturated olefins and/or polyunsaturated esters. The hydrogenating step may be conducted for 30-180 minutes at a temperature between 150° C. and 250° C. with a hydrogen gas pressure between 50 psig and 500 psig. In some embodiments, the hydrogenation catalyst has been recycled prior to the hydrogenating step.

In certain embodiments, the method further comprises treating the feedstock, prior to reacting the feedstock in the presence of a metathesis catalyst, under conditions sufficient to diminish catalyst poisons in the feedstock. In some embodiments, the treating step involves chemically treated through a chemical reaction to diminish the catalyst poisons. In other embodiments, the treating step involves treating the feedstock with one or more of the following: heat, molecular sieves, alumina, silica gel, montmorillonite clay, fuller's earth, bleaching clay, diatomaceous earth, zeolites, kaolin, activated metals, acid anhydrides, activated carbon, soda ash, metal hydrides, metal sulfates, metal halides, metal carbonates, metal silicates, phosphorous pentoxide, metal aluminum hydrides, alkyl aluminum hydrides, metal borohydrides, organometallic reagents, palladium on carbon catalysts, and combinations thereof. In yet other embodiments, the feedstock is heated to a temperature greater than 100° C. in the absence of oxygen and held at the temperature for a time sufficient to diminish the catalyst poisons.

In some embodiments, the method further comprises providing a low-molecular-weight olefin or a mid-weight olefin, wherein the reacting step comprises a cross-metathesis reaction between the feedstock with the low-molecular-weight olefin or mid-weight olefin.

In another embodiment, the method comprises providing a feedstock comprising polyunsaturated olefins and partially hydrogenating the polyunsaturated olefins in the presence of a hydrogenation catalyst for 30-180 minutes at a temperature between 150° C. and 250° C. with a hydrogen gas pressure between 50 psig and 500 psig, wherein the hydrogenation catalyst is provided in an amount between 0.01-1.0 wt % of the polyunsaturated olefins, wherein the hydrogenating step has a conversion rate of at least 85% and a selectivity of at least 90%. In some embodiments, the feedstock is treated prior to the hydrogenating step under conditions sufficient to diminish catalyst poisons in the feedstock. In other embodiments, the hydrogenation catalyst comprises a metal selected from the group consisting of nickel, copper, palladium, platinum, molybdenum, iron, ruthenium, osmium, rhodium, iridium, and combinations thereof. In some embodiments, the conversion rate is at least 90% and the selectivity is at least 95%. In other embodiments, the conversion rate is at least 95% and the selectivity is at least 99%. In yet other embodiments, the hydrogenation catalyst has been recycled prior to the hydrogenating step.

In another embodiment, the method comprises providing a feedstock comprising polyunsaturated esters and partially hydrogenating the polyunsaturated esters in the presence of a hydrogenation catalyst for 30-180 minutes at a temperature between 150° C. and 250° C. with a hydrogen gas pressure between 50 psig and 500 psig, wherein the hydrogenation catalyst is provided in an amount between 0.01-1.0 wt % of the polyunsaturated esters, wherein the hydrogenating step has a conversion rate of at least 85% and a selectivity of at least 90%. In some embodiments, the feedstock is treated prior to the hydrogenating step under conditions sufficient to diminish catalyst poisons in the feedstock. In other embodiments, the hydrogenation catalyst comprises a metal selected from the group consisting of nickel, copper, palladium, platinum, molybdenum, iron, ruthenium, osmium, rhodium, iridium, and combinations thereof. In some embodiments, the conversion rate is at least 90% and the selectivity is at least 95%. In other embodiments, the conversion rate is at least 95% and the selectivity is at least 99%. In yet other embodiments, the hydrogenation catalyst has been recycled prior to the hydrogenating step.

BRIEF DESCRIPTION OF THE DRAWINGS

FIG. 1 is a schematic diagram of one embodiment of a process to produce a fuel composition and a transesterified product from a natural oil.

DETAILED DESCRIPTION

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, the following terms have the following meanings unless expressly stated to the contrary. It is understood that any term in the singular may include its plural counterpart and vice versa.

As used herein, the term "metathesis catalyst" includes any catalyst or catalyst system that catalyzes a metathesis reaction.

As used herein, the terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

As used herein, the term "natural oil derivatives" may refer to the compounds or mixture of compounds derived from the natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9, 12-octadecadienoic acid), and linolenic acid (9,12,15-octadecatrienoic acid).

As used herein, the terms "metathesize" and "metathesizing" may refer to the reacting of a feedstock in the presence of a metathesis catalyst to form a "metathesized product" comprising a new olefinic compound. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the terms "ester" and "esters" may refer to compounds having the general formula: R—COO—R', wherein R and R' denote any organic compound (such as alkyl, aryl, or silyl groups), including those bearing heteroatom containing substituent groups. In certain embodiments, R and R' denote alkyl, alkenyl, aryl, or alcohol groups. In certain embodiments, the term "ester" or "esters" may refer to a group of compounds with the general formula described above, wherein the compounds have different carbon lengths.

As used herein, the term "dibasic ester" may refer to compounds having the general formula R'—OOC—Y—COO—R", wherein Y, R', and R" denote any organic compound (such as alkyl, aryl, or silyl groups), including those bearing heteroatom containing substituent groups. In certain embodiments, Y is a saturated or unsaturated hydrocarbon, and R' and R" are alkyl, alkenyl, aryl, or alcohol groups.

As used herein, the term "dibasic acid" may refer to compounds having the general formula R'—OOC—Y—COO—R", wherein R' and R" are hydrogen, and Y denotes any organic compound (such as an alkyl, alkenyl, aryl, alcohol, or silyl group), including those bearing heteroatom substituent groups. In certain embodiments, Y is a saturated or unsaturated hydrocarbon.

As used herein, the terms "olefin" and "olefins" may refer to hydrocarbon compounds having at least one unsaturated carbon-carbon double bond. In certain embodiments, the term "olefin" or "olefins" may refer to a group of unsaturated carbon-carbon double bond compounds with different carbon lengths. Unless noted otherwise, the term "olefin" or "olefins" encompasses "polyunsaturated olefins" or "poly-olefins" having more than one carbon-carbon double bond.

As used herein, the term "monounsaturated olefins" or "mono-olefins" refers to hydrocarbon compounds having only one carbon-carbon double bond.

It is noted that an olefin (including both mono- and polyolefins) may also comprise an ester, and an ester may also comprise an olefin, if the R or R' group in the general formula R—COO—R' contains an unsaturated carbon-carbon double bond. For example, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, alkenyl, alcohol or silyl group) and R has an olefin positioned at the end of the chain, and the term "internal olefin" may refer to an ester or an acid thereof where R' denotes hydrogen or any organic compound (such as an alkyl, aryl, alkenyl, alcohol, or silyl group) and R has an olefin positioned at an internal location on the chain.

As used herein, the term "low-molecular-weight olefin" may refer to any one or combination of unsaturated straight, branched, or cyclic hydrocarbons in the C2 to C14 range. Low-molecular-weight olefins include "alpha-olefins" or "terminal olefins," wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the C4 to C14 range. Examples of low-molecular-weight olefins in the C2 to C6 range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the C7 to C9 range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the C4-C10 range. In one embodiment, it may be preferable to use a mixture of linear and branched C4 olefins (i.e., combinations of: 1-butene, 2-butene, and/or isobutene). In other embodiments, a higher range of C11-C14 may be used.

As used herein, the term "mid-weight olefin" may refer to any one or combination of unsaturated straight, branched, or cyclic hydrocarbons in the C15 to C24 range. Mid-weight olefins include "alpha-olefins" or "terminal olefins," wherein the unsaturated carbon-carbon bond is present at one end of the compound. Mid-weight olefins may also include dienes or trienes. Mid-weight olefins may also include internal olefins or "mid-weight internal olefins." In certain embodiments, it is preferable to use a mixture of olefins.

As used herein, the terms "paraffin" and "paraffins" may refer to hydrocarbon compounds having only single carbon-carbon bonds, having the general formula $C_nH_{2n+2}$, where, in certain embodiments, n is less than about 20.

As used herein, the terms "isomerization," "isomerizes," or "isomerizing" may refer to the reaction and conversion of straight-chain hydrocarbon compounds, such as normal paraffins, into branched hydrocarbon compounds, such as iso-paraffins. In other embodiments, the isomerization of an olefin or an unsaturated ester indicates the shift of the carbon-carbon double bond to another location in the molecule (e.g., conversion from 9-decenoic acid to 8-decenoic acid), or it indicates a change in the geometry of the compound at the carbon-carbon double bond (e.g., cis to trans). As a non-limiting example, n-pentane may be isomerized into a mixture of n-pentane, 2-methylbutane, and 2,2-dimethylpropane. Isomerization of normal paraffins may be used to improve the overall properties of a fuel composition. Additionally, isomerization may refer to the conversion of branched paraffins into further, more branched paraffins.

As used herein, the term "yield" may refer to the total weight of product made from the metathesis and hydrogenation reactions. It may also refer to the total weight of the product following a separation step and/or isomerization reaction. It may be defined in terms of a yield %, wherein the total weight of the product produced is divided by the total weight of the natural oil feedstock and, in some embodiments, low-molecular-weight olefin and/or mid-weight olefin, combined.

As used herein, the terms "fuels" and "fuel compositions" refer to materials meeting required specifications or to blend components that are useful in formulating fuel compositions but, by themselves, do not meet all of the required specifications for a fuel.

As used herein, the term "carbon number distribution" may refer to the range of compounds present in a composition, wherein each compound is defined by the number of carbon atoms present. As a non-limiting example, a naphtha-type jet fuel typically comprises a distribution of hydrocarbon compounds wherein a majority of those compounds have between 5 and 15 carbon atoms each. A kerosene-type jet fuel typically comprises a distribution of hydrocarbon compounds wherein a majority of those compounds have between 8 and 16 carbon atoms each. A diesel fuel typically comprises a distribution of hydrocarbon compounds wherein a majority of those compounds have between 8 and 25 carbon atoms each.

As used herein, the term "diene-selective hydrogenation" or "selective hydrogenation" may refer to the targeted transformation of polyunsaturated olefins and/or esters to monounsaturated olefins and/or esters. One non-limiting example includes the selective hydrogenation of 3,6-dodecadiene to a mixture of monounsaturated products such as 1-dodecene, 2-dodecene, 3-dodecene, 4-dodecene, 5-dodecene, and/or 6-dodecene.

As used herein, the terms "conversion" and "conversion rate" may refer to the conversion from polyunsaturated olefins and/or esters into saturated esters, paraffins, monounsaturated olefins, and/or monounsaturated esters. In other words, conversion=(total polyunsaturates in the feedstock−total polyunsaturates in the product)/total polyunsaturates in the feed.

As used here, the term "selectivity" may refer to the distribution of monounsaturates formed in the hydrogenation step in comparison to paraffins and/or saturated esters. In other words, selectivity=total monounsaturates in product (total monounsaturates in product+total saturates in the product).

As mentioned above, the terminal olefin and internal olefin may be derived from a natural oil feedstock, in addition to other valuable compositions. A number of valuable compositions may be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions may include fuel compositions, detergents, surfactants, and other specialty chemicals. Non-limiting examples of fuel compositions include jet, kerosene, and diesel fuel. Additionally, transesterified products (i.e., the products formed from transesterifying an ester in the presence of an alcohol) may also be targeted, non-limiting examples of which include: fatty acid methyl esters; biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

In certain embodiments, prior to a metathesis reaction, a natural oil feedstock may be treated to render the natural oil more suitable for the subsequent metathesis reaction. In certain embodiments, the natural oil preferably is a vegetable oil or vegetable oil derivative, such as soybean oil.

In one embodiment, the treatment of the natural oil involves the removal of catalyst poisons, such as peroxides, which may potentially diminish the activity of the metathesis catalyst. Non-limiting examples of natural oil feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the natural oil feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the natural oil feedstock with nitrogen, wherein the nitrogen gas is pumped into the feedstock treatment vessel at a pressure of approximately 10 atm (150 psig).

In certain embodiments, the natural oil feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfite, borohydride, phosphine, thiosulfate, individually or combinations thereof.

In certain embodiments, the natural oil feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the natural oil feedstock's reactivity with the metathesis catalyst. Additional non-limiting examples of feedstock treatment are also described below when discussing the various metathesis catalysts.

In some embodiments, the natural oil feedstock is treated with a first agent, second agent, third agent, and/or any additional agents to remove the catalyst poisons. The first, second, third, and/or any additional agents may be individually selected from the group consisting of heat, molecular sieves, alumina (aluminum oxide), silica gel, montmorillonite clay, fuller's earth, bleaching clay, diatomaceous earth (e.g., as sold under the trade name CELITE), zeolites, kaolin, activated metals (e.g., Cu, Mg, and the like), acid anhydrides (e.g., acetic anhydride "$Ac_2O$" and the like) activated carbon (a.k.a., activated charcoal), soda ash, metal hydrides (e.g., alkaline earth metal hydrides such as $CaH_2$ and the like), metal sulfates (e.g., alkaline earth metal sulfates such as calcium sulfate, magnesium sulfate, and the like; alkali metal sulfates such as potassium sulfate, sodium sulfate, and the like; and other metal sulfates such as aluminum sulfate, potassium magnesium sulfate, and the like), metal halides (e.g., alkali earth metal halides such as potassium chloride and the like), metal carbonates (e.g., calcium carbonate, sodium carbonate, and the like), metal silicates (e.g., magnesium silicate and the like), phosphorous pentoxide, metal aluminum hydrides (e.g., alkali metal aluminum hydrides such as $LiAlH_4$, $NaAlH_4$ and the like), alkyl aluminum hydrides (e.g., $iBu_2AlH$ a.k.a. DIBALH), metal borohydrides (e.g., alkali metal borohydrides such as $LiBH_4$, $NaBH_4$, and the like), metal alkoxides, organometallic reagents (e.g., Grignard reagents; organolithium reagents such as n-butyl lithium, t-butyl lithium, sec-butyl lithium; trialkyl aluminums such as triethyl aluminum ("$Et_3Al$"), tributyl aluminum, triisopropyl aluminum, trioctyl aluminum ("$Oc_3Al$"), and the like, metal amides (e.g., lithium diisopropyl amide a.k.a. LDA, metal bis(trimethylsilyl)amides such as KHMDS, and the like), palladium on carbon (Pd/C) catalysts, and combinations thereof.

In certain embodiments, the first agent, second agent, third agent, and/or any additional agents used in accordance with the present teachings are each individually selected from the group consisting of heat, optionally heat-treated molecular sieves, optionally heat-treated alumina (e.g., activated, acidic, basic, and neutral), optionally heat-treated silica gel, montmorillonite clay, fuller's earth, bleaching clay, diatomaceous earth (e.g., as sold under the trade name CELITE), zeolites, kaolin, activated metals, acid anhydrides, activated carbon, soda ash, metal hydrides, metal sulfates, metal halides, metal carbonates, metal silicates, phosphorous pentoxide, metal aluminum hydrides, alkyl aluminum hydrides, metal borohydrides, metal alkoxides, organometallic reagents, metal amides, and the like, and combinations thereof.

In some embodiments, the first agent, second agent, third agent, and/or any additional agents used in accordance with the present teachings are each individually selected from the group consisting of optionally heat-treated activated molecular sieves, optionally heat-treated activated alumina, optionally heat-treated activated acidic alumina, optionally heat-treated activated neutral alumina, optionally heat-treated activated basic alumina, alkaline earth metal hydrides, alkaline earth metal sulfates, alkali metal sulfates, alkali earth metal halides, alkali metal aluminum hydrides, alkali metal borohydrides, aluminum alkoxides, titanium alkoxides, zirconium alkoxides, copper alkoxides, iron alkoxides, cerium alkoxides, silicon alkoxides, Grignard reagents; organolithium reagents, trialkyl aluminums, metal bis(trimethylsilyl)amides, and the like, and combinations thereof.

In some embodiments, the first agent, second agent, third agent, and/or any additional agents used in accordance with the present teachings are each individually selected from the group consisting of $CaH_2$, activated Cu, activated Mg, acetic anhydride, calcium sulfate, magnesium sulfate, potassium sulfate, aluminum sulfate, potassium magnesium sulfate, sodium sulfate, calcium carbonate, sodium carbonate, magnesium silicate, potassium chloride, lithium aluminum hydride, sodium aluminum hydride, triisobutylaluminum hydride, metal methoxide, metal ethoxide, metal n-propoxide, metal isopropoxide, metal butoxide, metal 2-methylpropoxide, metal tert-butoxide, titanium isopropoxide, aluminum ethoxide, aluminum isopropoxide, zirconium ethoxide, and combinations thereof, n-butyl lithium, t-butyl lithium, sec-butyl lithium, triethyl aluminum, tributyl aluminum, triisopropyl aluminum, triisobutyl aluminum, trioctyl aluminum, lithium diisopropyl amide, potassium hexamethyldisilazane (KHMDS), and the like, and combinations thereof.

In some embodiments, the first agent, second agent, third agent, and/or any additional agents used in accordance with the present teachings are each individually and optionally attached to a solid support. Representative solid supports for use in accordance with the present teachings include but are not limited to carbon, silica, silica-alumina, alumina, clay, magnesium silicates (e.g., Magnesols), the synthetic silica adsorbent sold under the trade name TRISYL by W. R. Grace & Co., diatomaceous earth, polystyrene, macroporous (MP) resins, and the like, and combinations thereof.

Typically, there are several choices of different and oftentimes complementary agents from which to choose when preparing to treat a contaminated feedstock prior to a metathesis reaction. While neither desiring to be bound by any particular theory nor intending to limit in any measure the scope of the appended claims or their equivalents, it is presently believed that the following non-exhaustive and non-limiting list of representative treatment methodologies can be useful in treating feedstocks that contain the specified contaminants (provided the agents are compatible with any functional groups on the feedstock and/or with the contaminants themselves, etc.): (a) a thermal treatment—for example, heating (and/or distilling) a feedstock (e.g., between about 100° C. and about 250° C., or around 200° C. in some embodiments—depending on the feedstock's boiling point, optionally with a purge of an inert gas such as $N_2$ and/or the like) and/or treatment with an adsorbent (e.g., alumina and the like) can be useful in decomposing peroxide contaminants and/or decomposition products thereof; (b) treatment with an acid anhydride (e.g., acetic anhydride, $Ac_2O$) can be useful in removing moisture, active hydroxyl-containing materials (e.g., alcohols), and hydroperoxides (via acetylation); (c) treatment with a desiccant (e.g., silica gel, alumina, molecular sieves, magnesium sulfate, calcium sulfate, and the like, and combinations thereof) and/or an organometallic reagent (e.g., t-butyl lithium, triethyl aluminum, tributyl aluminum, triisopropyl aluminum, trioctyl aluminum, and the like, and combinations thereof) and/or metal hydrides (e.g., $CaH_2$ and the like) and/or acid anhydrides (e.g., acetic anhydride and the like) can be useful in removing moisture; (d) treatment with an adsorbent (e.g., alumina, silica gel, and the like, and combinations thereof) and/or an organometallic reagent (e.g., t-butyl lithium, triethyl aluminum, tributyl aluminum, triisopropyl aluminum, trioctyl aluminum, and the like, and combinations thereof) and/or a metal amide (e.g., LDA, KHMDA, and the like) can be useful in removing protic materials; (e) treatment with an adsorbent (e.g., alumina, silica gel, activated charcoal, and the like, and combinations thereof) can be useful in removing polar materials; (f) treatment with an organometallic reagent (e.g., (e.g., t-butyl lithium, triethyl aluminum, tributyl aluminum, triisopropyl aluminum, trioctyl aluminum, and the like, and combinations thereof) can be useful in removing Lewis basic catalyst poisons; etc.

In some embodiments, the first agent used to treat a feedstock prior to a metathesis reaction comprises an adsorbent which, in some embodiments, is selected from the group consisting of silica gel, alumina, bleaching clay, activated carbon, molecular sieves, zeolites, fuller's earth, diatomaceous earth, and the like, and combinations thereof. In some embodiments, the first agent is selected from the group consisting of optionally heat-treated molecular sieves, optionally heat-treated alumina, and a combination thereof. In some embodiments, the adsorbent comprises optionally heat-treated activated alumina which, in some embodiments, is selected from the group consisting of optionally heat-treated activated acidic alumina, optionally heat-treated activated neutral alumina, optionally heat-treated activated basic alumina, and combinations thereof. In some embodiments, the absorbent comprises optionally heat-treated activated neutral alumina, which can be useful in treating feedstocks (e.g., olefins) that are susceptible to acid-catalyzed isomerization and/or rearrangement.

For embodiments in which the first agent, second agent, third agent, and/or any additional agents used in accordance with the present teachings comprises an adsorbent (e.g., molecular sieves, alumina, etc.), it is presently believed that the treating of the feedstock with the adsorbent is more effectively performed by flowing the feedstock through the first agent using a percolation- or flow-type system (e.g., chromatography column) as opposed to simply adding the adsorbent to the feedstock at the bottom of a container. In some embodiments, about 20 wt % of alumina is used in a column. While neither desiring to be bound by any particular theory nor intending to limit in any measure the scope of the appended claims or their equivalents, it is presently believed that treating a feedstock with alumina on about a 5-to-1 weight-to-weight basis is effective for some embodiments. However, it is to be understood that the amount of alumina used is not restricted and will be both feedstock- and impurity dependent in addition to being impacted by the form of the alumina, its activation process, and the precise treatment method (e.g., flow through a column vs. direct addition to container).

In some embodiments, the first agent, second agent, third agent, and/or any additional agents used to treat a feedstock prior to a metathesis reaction comprises a trialkyl aluminum which, in some embodiments, is selected from the group consisting of triethyl aluminum, tributyl aluminum, triisopropyl aluminum, trioctyl aluminum, triisobutyl aluminum and the like, and combinations thereof. While neither desiring to be bound by any particular theory nor intending to limit in any measure the scope of the appended claims or their equivalents, it is presently believed that in some cases the treatment of a feedstock with a trialkyl aluminum greatly improves feedstock conversions at low concentrations of metathesis catalyst but that in the presence of excess trialkyl aluminum, catalyst performance is adversely affected. Thus, in some embodiments (e.g., when a trialkyl aluminum is used as a first agent and/or an excess of trialkyl aluminum is used), a successive agent used to treat the feedstock can comprise an adsorbent which can remove excess trialkyl aluminum. In other embodiments, the amount of trialkyl aluminum used for treatment of the feedstock can be reduced by first treating the feedstock with a different agent of a type described herein (e.g., an adsorbent including but not limited to molecular sieves, alumina, and/or the like), and then introducing the trialkyl aluminum as a second (or subsequent) agent to remove residual contaminants. In any event, while neither desiring to be bound by any particular theory nor intending to limit in any measure the scope of the appended claims or their equivalents, it is presently believed that removal of excess trialkyl aluminum from organic products should be performed with great caution since use of the wrong adsorbent might lead to a highly exothermic reaction or a highly unstable species. In some embodiments, the trialkylaluminum is attached to a solid support to simplify its removal.

In some embodiments, molecular sieves can be used as a first agent for bulk drying a feedstock, "high heat-treated" alumina can then be used as a second agent to remove additional moisture, and finally molecular sieves can be used at the end as a third agent for removing still further residual moisture. In other embodiments, molecular sieves can be used as a first agent for bulk drying a feedstock, "high heat-treated" alumina can then be used as a second agent to remove additional moisture, and finally a trialkyl aluminum (e.g., triethyl aluminum, tributyl aluminum, triisopropyl aluminum, trioctyl aluminum, triisobutyl aluminum and the like, and combinations thereof) can be used as a third agent for removing any further residual moisture.

In one particular embodiment, activated copper powder is used alone or in combination with another treatment. For example, in some embodiments, activated copper powder is used in combination with heat (e.g., 200° C. for at least 2 hours under nitrogen gas), molecular sieves, and/or a trialkylaluminum treatment. In another embodiment, activated magnesium tunings are used alone or in combination with another treatment. For example, in some embodiments, activated magnesium tunings are used in combination with heat (e.g., 200° C. for at least 2 hours under nitrogen gas), molecular sieves, and/or a trialkylaluminum treatment.

In another particular embodiment, acetic anhydride is used alone or in combination with another treatment/agent. For example, in some embodiments, acetic anhydride is used in combination with alumina (aluminum oxide) and/or a trialkylaluminum treatment. In other embodiments, acetic anhydride is used in combination with alumina, distillation, molecular sieves, and/or a trialkylaluminum treatment. Further, percolation on activated alumina or molecular sieves can be applied before or instead of the triaklyaluminum treatment.

In another embodiment, alumina is used alone or in combination with another treatment/agent. In one embodiment, alumina is used in combination with a palladium on carbon (Pd/C) catalyst and/or a trialkylaluminum treatment.

Additionally, in certain embodiments, the low-molecular-weight olefin or mid-weight olefin may also be treated prior to the metathesis reaction with the natural oil. Like the natural oil treatment, the low-molecular-weight olefin or mid-weight olefin may be treated to remove poisons that may impact or diminish catalyst activity using any of the above-mentioned methods of treatment.

In certain embodiments, the low-molecular-weight olefin or mid-weight olefin may be self-metathesized to form a metathesized low-molecular-weight olefin or metathesized mid-weight olefin in order to adjust the properties of the olefin and the potential products following metathesis with the natural oil. In some embodiments, the low-molecular-weight olefin or mid-weight olefin is self-metathesized in the presence of a rhenium oxide catalyst (e.g., rhenium oxide supported on alumina) or tungsten oxide catalyst (e.g., tungsten oxide supported on silica). This reaction may be conducted in a fixed bed reactor. In one embodiment, the low-molecular-weight olefin is 1-butene. The low-molecular-weight olefin may be self-metathesized over rhenium oxide catalyst in a fixed bed reactor to produce mainly 3-hexene and ethylene. Ethylene may be separated from the reactor effluent for further processing, such as being sent to an ethylene purification system or ethylene oxide system. Unreacted low-molecular-weight olefin (e.g., 1-butene) may be recycled to the fixed bed reactor and the metathesized low-weight-olefin (e.g., 3-hexene) may be sent to the metathesis reactor for metathesis with the natural oil.

In other embodiments, the low-molecular-weight olefin or mid-weight olefin is isomerized prior to being metathesized with the natural oil. Adjusting the composition and properties of the low-molecular-weight olefin or mid-weight olefin through isomerization may allow for different products or different ratios of products to be formed following metathesis of the low-molecular-weight olefin or mid-weight olefin with a natural oil. In some embodiments, the isomerized or branched low-molecular-weight olefin is in the C4 to C10 range. In one embodiment, hexene is isomerized to form a branched low-molecular-weight olefin. Non-limiting examples of branched low-molecular-weight olefins include isobutene, 3-methyl-1-butene, 2-methyl-3-pentene, and 2,2-dimethyl-3-pentene.

By using branched low-molecular-weight olefins or branched mid-weight olefins in the metathesis reaction, the metathesized product will include branched olefins, which can be subsequently hydrogenated to iso-paraffins. In certain embodiments, the branched low-molecular-weight olefins or branched mid-weight olefins may help achieve the desired performance properties for a fuel composition, such as jet, kerosene, or diesel fuel. In certain embodiments, C11-C14 olefins may be targeted following metathesis and separation steps through isomerization of the low-molecular-weight olefin. In other embodiments, the branched low-molecular-weight olefins or branched mid-weight olefins may help target longer chain esters for use as detergents or cleaning compositions. In some embodiments, C10-C15 or C11-C14 methyl esters may be targeted following metathesis, separation, and transesterification steps (discussed in detail below).

Isomerization reactions are well-known in the art, as described in U.S. Pat. Nos. 3,150,205; 4,210,771; 5,095,169; and 6,214,764, herein incorporated by reference in their entireties.

As shown in FIG. 1, after this optional treatment of the natural oil feedstock, low-molecular-weight olefin, and/or mid-weight olefin, the natural oil 12 is reacted with itself, or combined with a low-molecular-weight olefin 14 or mid-weight olefin 15 in a metathesis reactor 20 in the presence of a metathesis catalyst. Metathesis catalysts and metathesis reaction conditions are discussed in greater detail below. In certain embodiments, in the presence of a metathesis catalyst, the natural oil 12 undergoes a self-metathesis reaction with itself. In other embodiments, in the presence of the metathesis catalyst, the natural oil 12 undergoes a cross-metathesis reaction with the low-molecular-weight olefin 14 or mid-weight olefin 15. In certain embodiments, the natural oil 12 undergoes both self- and cross-metathesis reactions in parallel metathesis reactors. The self-metathesis and/or cross-metathesis reaction form a metathesized product 22 wherein the metathesized product 22 comprises olefins 32 and esters 34.

In certain embodiments, the low-molecular-weight olefin 14 is in the C2 to C6 range. As a non-limiting example, in one embodiment, the low-molecular-weight olefin 14 may comprise at least one of the following: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the C7 to C9 range include 1,4-heptadiene, 1-heptene, 3,6-nonadiene, 3-nonene, 1,4,7-octatriene. In another embodiment, the low-molecular-weight olefin 14 comprises at least one of styrene and vinyl cyclohexane. In another embodiment, the low-molecular-weight olefin 14 may comprise at least one of ethylene, propylene, 1-butene, 2-butene, and isobutene. In another embodiment, the low-molecular-weight olefin 14 comprises at least one alpha-olefin or terminal olefin in the C2 to C10 range.

In another embodiment, the low-molecular-weight olefin 14 comprises at least one branched low-molecular-weight olefin in the C4 to C10 range. Non-limiting examples of branched low-molecular-weight olefins include isobutene, 3-methyl-1-butene, 2-methyl-3-pentene, and 2,2-dimethyl-3-pentene.

In certain embodiments, the mid-weight olefin 15 comprises unsaturated straight, branched, or cyclic hydrocarbons in the C15 to C24 range. In some embodiments, the mid-weight olefin is an alpha-olefin or terminal olefin.

As noted, it is possible to use a mixture of various linear or branched low-molecular-weight olefins and linear or branched mid-weight olefins in the reaction to achieve the desired metathesis product distribution. In certain embodiments, the mixture comprises linear and/or branched low-molecular-weight olefins. In other embodiments, the mixture comprises linear and/or branched mid-weight olefins. In one embodiment, a mixture of butenes (1-butene, 2-butenes, and, optionally, isobutene) may be employed as the low-molecular-weight olefin, offering a low cost, commercially available feedstock instead a purified source of one particular butene. Such low cost mixed butene feedstocks are typically diluted with n-butane and/or isobutane.

In certain embodiments, recycled streams from downstream separation units may be introduced to the metathesis reactor 20 in addition to the natural oil 12 and, in some embodiments, the low-molecular-weight olefin 14 and/or mid-weight olefin 15. For instance, in some embodiments, a C2-C6 recycle olefin stream or a C3-C4 bottoms stream from an overhead separation unit may be returned to the metathesis reactor. In one embodiment, as shown in FIG. 1, a light weight olefin stream 44 from an olefin separation unit 40 may be returned to the metathesis reactor 20. In another embodiment, the C3-C4 bottoms stream and the light weight olefin stream 44 are combined together and returned to the metathesis reactor 20. In another embodiment, a C15+ bottoms stream 46 from the olefin separation unit 40 is returned to the metathesis reactor 20. In another embodiment, all of the aforementioned recycle streams are returned to the metathesis reactor 20. In another embodiment, one or more of the recycle streams may be selectively hydrogenated to increase the concentration of mono-olefins in the stream.

In other embodiments, various ester streams downstream of the transesterification unit (discussed below) may also be recycled or returned to the metathesis reactor 20. In certain embodiments, a glycerolysis reaction may be conducted on the recycled ester stream to prevent or limit the amount of free glycerol entering the metathesis reactor 20. In some embodiments, the recycled ester stream will undergo a purification step to limit the amount of methanol being recycled to the metathesis reactor 20. In some embodiments, the recycled ester stream is combined with the low-molecular-weight olefin 14 and/or mid-weight olefin 15 prior to conducting the glycerolysis reaction and entering the metathesis reactor 20. In another embodiment, the recycled ester stream may be partially or selectively hydrogenated to increase the concentration of monounsaturated esters in the stream. The glycerolysis reaction may also limit or prevent free fatty acid methyl esters from entering the metathesis reaction and subsequently exiting the metathesis reactor as free fatty acid methyl esters that may boil close to various high-valued olefin products. In such cases, these methyl ester components may be separated with the olefins during the separation of the olefins and esters. Such methyl ester components may be difficult to separate from the olefins by distillation.

The metathesis reaction in the metathesis reactor 20 produces a metathesized product 22. In one embodiment, the metathesized product 22 enters a flash vessel operated under temperature and pressure conditions which cause C2 or C2-C3 compounds to flash off and be removed overhead. The C2 or C2-C3 light ends are comprised of a majority of hydrocarbon compounds having a carbon number of 2 or 3. In certain embodiments, the C2 or C2-C3 light ends are then sent to an overhead separation unit, wherein the C2 or C2-C3 compounds are further separated overhead from the heavier compounds that flashed off with the C2-C3 compounds. These heavier compounds are typically C3-C5 compounds carried overhead with the C2 or C2-C3 compounds. After separation in the overhead separation unit, the overhead C2 or C2-C3 stream may then be used as a fuel source. These hydrocarbons have their own value outside the scope of a fuel composition, and may be used or separated at this stage for other valued compositions and applications. In certain embodiments, the bottoms stream from the overhead separation unit containing mostly C3-C5 compounds is returned as a recycle stream to the metathesis reactor. In the flash vessel, the metathesized product 22 that does not flash overhead is sent downstream for separation in a separation unit 30, such as a distillation column.

Prior to the separation unit 30, in certain embodiments, the metathesized product 22 may be contacted with a reactant or reagent to deactivate or to extract the catalyst. In certain embodiments, the metathesized product 22 is introduced to an adsorbent or complexing agent to facilitate the separation of the metathesized product 22 from the metathesis catalyst. In one embodiment, the adsorbent or complexing agent is a clay bed. The clay bed will adsorb the metathesis catalyst, and after a filtration step, the metathesized product 22 can be sent to the separation unit 30 for further processing. In another embodiment, the adsorbent or complexing agent is a water soluble phosphine reagent such as tris hydroxymethyl phosphine (THMP). Catalyst may be separated with a water soluble phosphine through known liquid-liquid extraction mechanisms by decanting the aqueous phase from the organic phase.

In some embodiments, the metathesized product 22 may be sent to a catalyst kill drum where the reagent (e.g., THMP aqueous solution) is added to deactivate the metathesis catalyst. THMP may be added at a rate equivalent to at least 1:1, 5:1, 10:1, 25:1, or 50:1 molar ratio relative to the catalyst pumped into the catalyst kill drum.

In certain embodiments, the reagent (e.g., THMP) can be left in the metathesized product 22 and carried along, either in whole or in part, into a subsequent chemical reaction or processing step. In other embodiments, the reagent can be separated and removed from the mixture, either partially or completely, prior to any subsequent reaction or processing step. In some embodiments, passivation and extraction can be coupled into one step (e.g., by providing the reagent in the extracting material).

In one embodiment, the catalyst separation occurs by sending the effluent from the catalyst kill drum to a catalyst decanter drum. The decanter drum may function as a horizontal vessel with a vertical baffle and a boot to collect the water phase containing the metathesis catalyst. In some embodiments, the decanter drum operates at a temperature between approximately 60-90° C. and a pressure between 1-1.5 atm, or approximately 53° C. (127° F.) and 1.1 atm (16 psia).

In other embodiments, the catalyst separation comprises washing or extracting the mixture with a polar solvent (e.g., particularly, though not exclusively, for embodiments in which the reagent is at least partially soluble in the polar solvent). In some embodiments, the polar solvent is added in a subsequent step following catalyst deactivation. In other embodiments, the polar solvent (e.g., water) is added to the metathesized product 22 at approximately the same time as the deactivation reagent (e.g., THMP). Near simultaneous addition of the deactivation reagent and polar solvent to the metathesized product can eliminate the need for an additional reaction/separation vessel, which may simply the process and potentially save capital.

In some embodiments, the polar solvent is at least partially non-miscible with the mixture, such that a separation of layers can occur. In some embodiments, at least a portion of the reagent is partitioned into the polar solvent layer, which can then be separated from the non-miscible remaining layer and removed. Representative polar solvents for use in accordance with the present teachings include but are not limited to water, alcohols (e.g., methanol, ethanol, etc.), ethylene glycol, glycerol, DMF, multifunctional polar compounds including but not limited to polyethylene glycols and/or glymes, ionic liquids, and the like, and combinations thereof. In some embodiments, the mixture is extracted with water. In some embodiments, when a phosphite ester that is at least partially hydrolyzable (e.g., in some embodiments, a phosphite ester having a low molecular weight, including but not limited to trimethyl phosphite, triethyl phosphite, and a combination thereof) is used as a reagent, washing the mixture with water may convert the phosphite ester into a corresponding acid. While neither desiring to be bound by any particular theory nor intending to limit in any measure the scope of the appended claims or their equivalents, it is presently believed that such a hydrolysis may occur more rapidly with lower molecular weight esters.

In some embodiments, when extraction with a polar solvent is desired, the extraction may comprise high shear mixing (e.g., mixing of a type sufficient to disperse and/or transport at least a portion of a first phase and/or chemical species into a second phase with which the first phase and/or a chemical species would normally be at least partly immiscible) although such mixing, in some embodiments, may contribute to undesirable emulsion formation. In some embodiments, the extracting comprises low-intensity mixing (e.g., stirring that is not high shear). The present teachings are in no way restricted to any particular type or duration of mixing. However, for purposes of illustration, in some embodiments, the extracting comprises mixing the polar solvent and the mixture together for at least about 1 second, 10 seconds, 30 seconds, 1 minute, 2 minutes, 5 minutes, 10 minutes, 15 minutes, 20 minutes, 25 minutes, 30 minutes, 35 minutes, 40 minutes, 45 minutes, 50 minutes, 55 minutes, or 60 minutes. While neither desiring to be bound by any particular theory nor intending to limit in any measure the scope of the appended claims or their equivalents, it is presently believed that shorter mixing times (e.g., on the order of a second or seconds) are achievable when inline shear mixing is used for mixing.

When extraction with a polar solvent is desired, the present teachings are in no way restricted to any particular amount of polar solvent added to the mixture for the extracting. However, for purposes of illustration, in some embodiments, the amount by weight of polar solvent (e.g., water) added to the mixture for the extracting is more than the weight of the mixture. In some embodiments, the amount by weight of polar solvent (e.g., water) added to the mixture for the extracting is less than the weight of the mixture. In some embodiments, the weight ratio of the mixture to the water added to the mixture is at least about 1:1, 2:1, 3:1, 4:1, 5:1, 6:1, 7:1, 8:1, 9:1, 10:1, 20:1, 40:1, or 100:1. For higher oil to water ratios, extraction and separation using a centrifuge and/or coalescer may be desirable.

In some embodiments, when extraction with a polar solvent is desired, methods for suppressing dehydrogenation in accordance with the present teachings further comprise allowing a settling period following the polar solvent wash to promote phase separation. The present teachings are in no way restricted to any particular duration of settling period. However, for purposes of illustration, in some embodiments, the settling period is at least about 1 minute, 2 minutes, 5 minutes, 10 minutes, 15 minutes, 30 minutes, 60 minutes, or 120 minutes.

In addition to or as an alternative to washing the mixture with a polar solvent to remove the reagent (e.g., THMP)—a method in accordance with the present teachings can optionally further comprise removing at least a portion of the reagent by adsorbing it onto an adsorbent, which optionally can then be physically separated from the mixture (e.g., via filtration, centrifugation, crystallization, or the like). In some embodiments, the adsorbent is polar. Representative adsorbents for use in accordance with the present teachings include but are not limited to carbon, silica, silica-alumina, alumina, clay, magnesium silicates (e.g., Magnesols), the synthetic silica adsorbent sold under the trade name TRISYL by W. R. Grace & Co., diatomaceous earth, polystyrene, macroporous (MP) resins, and the like, and combinations thereof.

Additionally, in certain embodiments, prior to the separation unit 30 (and after catalyst separation, in some instances), the metathesis product 22 may be sent to a hydrogenation unit, wherein the carbon-carbon double bonds in the olefins and esters are partially, selectively, or fully saturated with hydrogen gas. Hydrogenation may be conducted according to any known method in the art for hydrogenating double bond-containing compounds such as the olefins and esters present in the metathesis product 22. In certain embodiments, the metathesis product is partially or selectively hydrogenated to increase the concentration of monounsaturated olefins and/or ester compounds present in the metathesis product 22. In certain embodiments, in the diene selective hydrogenation, the conversion rate from the polyunsaturated olefins and esters to paraffins, saturated esters, monounsaturated olefins, and monounsaturated esters may be at least 50%, at least 75%, at least 85%, at least 95%, or at least 98%. The selectivity towards the monounsaturated olefins and monounsaturated esters instead of the paraffins and saturated esters is at least 90%, at least 95%, at least 99%, or at least 99.5%.

In certain embodiments, in the hydrogenation unit, hydrogen gas is reacted with the metathesis product 22 in the presence of a hydrogenation catalyst to produce a hydrogenated product comprising partially to fully hydrogenated paraffins/olefins and partially to fully hydrogenated esters.

In some embodiments, the metathesis product 22 is hydrogenated in the presence of a hydrogenation catalyst comprising nickel, copper, palladium, platinum, molybdenum, iron, ruthenium, osmium, rhodium, or iridium, individually or in combinations thereof. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts are characterized by a high nickel surface area per gram of nickel. Commercial examples of supported nickel hydrogenation catalysts include those available under the trade designations "NYSOFACT", "NYSOSEL", and "NI 5248 D" (from BASF Catalysts LLC, Iselin, N.J.). Additional supported nickel hydrogenation catalysts include those commercially available under the trade designations "PRICAT 9908", "PRICAT 9910", "PRICAT 9920", "PRICAT 9932, " "PRICAT 9936, " "PRICAT 9939, " "PRICAT 9953, " "PRICAT 20/15 D," "PRICAT NI 52/35 P," "PRICAT NI 55/5 P," "PRICAT NI 60/15 P," "PRICAT NI 62/15 P," "PRICAT NI 52/35 T," "PRICAT NI 55/5 T," and "PRICAT NI 60/15 T" (available from Johnson Matthey Catalysts, Ward Hill, Mass.) (wherein D=droplet, P=powder, and T=tablet). The supported nickel catalysts may be of the type described in U.S. Pat. Nos. 3,351,566, 6,846,772, EP 0168091, and EP 0167201, incorporated by reference herein in their entireties.

In other embodiments, the hydrogenation catalyst comprises copper that has been chemically reduced with hydrogen to an active state (i.e., reduced copper) provided on a support. The support may comprise porous silica (e.g., kieselguhr, infusorial, diatomaceous, or siliceous earth) or alumina. Commercial examples of supported copper hydrogenation catalysts include "PRICAT CU 60/8 T," "PRICAT CU 60/35 T," "PRICAT CU 50/8 P," and "PRICAT CU 60/35 P" (available from Johnson Matthey Catalysts, Ward Hill, Mass.) (wherein T=tablet and P=powder).

Hydrogenation may be carried out in a batch or in a continuous process and may be a partial, selective, or complete hydrogenation. In certain embodiments, the hydrogenation is a selective hydrogenation, wherein the polyunsaturated olefins or esters in the metathesis product 22 are selectively saturated to form compositions having higher amounts of monounsaturated olefins or esters, while limiting the amount of fully saturated hydrocarbons or saturated esters produced. In some embodiments, the partial or selective hydrogenation reaction may be conducted over a period of time ranging from 10-360 minutes, 20-240 minutes, 30-180 minutes, or 60-90 minutes.

In certain embodiments, the temperature at which the partial or selective hydrogenation step ranges from about 50° C. to about 350° C., about 100° C. to about 300° C., about 150° C. to about 250° C., about 100° C. to about 150° C., about 150° C., or about 180° C. The desired temperature may vary, for example, with hydrogen gas pressure. Typically, a higher gas pressure will require a lower temperature. Hydrogen gas is pumped into the reaction vessel to achieve a desired pressure of $H_2$ gas. In certain embodiments, the $H_2$ gas pressure ranges from about 15 psig (1 atm) to about 3000 psig (204.1 atm), about 15 psig (1 atm) to about 90 psig (6.1 atm), or about 50 psig (3.4 atm) to about 500 psig (34 atm). As the gas pressure increases, more specialized high-pressure processing equipment may be required. In certain embodiments, the reaction conditions are "mild," wherein the temperature is approximately between approximately 50° C. and approximately 100° C. and the $H_2$ gas pressure is less than approximately 100 psig. In other embodiments, the temperature is between about 100° C. and about 150° C., and the pressure is between about 50 psig (3.4 atm) and about 500 psig (34 atm). In some embodiments, the temperature is about 150° C. and the hydrogen gas pressure is about 100 psig (6.8 atm). In other embodiments, the temperature is about 180° C. and the hydrogen gas pressure is about 100 psig (6.8 atm). When the desired degree of hydrogenation is reached, the reaction mass is cooled to the desired filtration temperature.

The amount of hydrogenation catalyst is typically selected in view of a number of factors including, for example, the type of hydrogenation catalyst used, the amount of feed used, the degree of unsaturation in the material to be hydrogenated, the desired rate of hydrogenation, the desired degree of hydrogenation (e.g., as measured by iodine value (IV)), the selectivity of the hydrogenation, the purity of the reagent, and the $H_2$ gas pressure. In some embodiments, the hydrogenation catalyst is used in an amount of about 10 weight % or less, for example, about 5 weight % or less or about 1 weight % or less of the substrate being treated. In some embodiments, the amount of hydrogenation catalyst is between 0.01-1.0 wt %, between 0.02-0.5 wt %, or between 0.1-0.25 wt % of the substrate being treated (e.g., the metathesis product 22 or olefins 32, as described below).

In certain embodiments, the hydrogenation catalyst may be reused or recycled for a subsequent use or for multiple uses. In some embodiments, the hydrogenation catalyst is recycled once. In other embodiments, it is recycled two times, or three or more times.

When the desired degree of hydrogenation is reached, the reaction mass is cooled to the desired filtration temperature. During hydrogenation, the carbon-carbon double bonds are partially to fully saturated by the hydrogen gas. In one embodiment, the olefins in the metathesis product 22 are reacted with hydrogen to form a fuel composition comprising only or mostly paraffins. Additionally, the esters from the metathesis product are fully or nearly fully saturated in the hydrogenation unit. In other embodiment, the resulting hydrogenated product includes only partially saturated olefins and partially saturated esters. In some embodiments, the resulting selective hydrogenation product is comprised of an increased percentage of monounsaturated olefins and/or esters.

In the separation unit 30, in certain embodiments, the metathesized product 22 (from a hydrogenation unit, metathesis reactor 20, or catalyst separation unit) is separated into at least two product streams. In one embodiment, the metathesized product 22 is sent to the separation unit 30, or distillation column, to separate the olefins 32 from the esters 34. In another embodiment, a byproduct stream comprising $C_7$'s and cyclohexadienes (e.g., 1,4-cyclohexadiene) may be removed in a side-stream from the separation unit 30. In certain embodiments, the separated olefins 32 may comprise hydrocarbons with carbon numbers up to 24. In certain embodiments, the esters 34 may comprise metathesized glycerides. In other words, the lighter end olefins 32 are preferably separated or distilled overhead for processing into olefin compositions, while the esters 34, comprised mostly of compounds having carboxylic acid/ester functionality, are drawn into a bottoms stream. Based on the quality of the separation, it is possible for some ester compounds to be carried into the overhead olefin stream 32, and it is also possible for some heavier olefin hydrocarbons to be carried into the ester stream 34. Additionally, the separated cyclohexadienes (e.g., 1,4-cyclohexadiene) may be further processed in a dehydrogenation step to form benzene. Examples of catalytic dehydrogenation catalysts include platinum supported on alumina. Examples of oxidative dehydrogenation catalysts include mixed metal oxides consisting of molybdenum, vanadium, niobium, tellurium, magnesium, and/or aluminum. Other dehydrogenation catalysts examples include cerium/zirconium, alkaline earth/nickel, calcium-nickel-phosphate, chromium, iron-chromium oxide, bismuth/molybdenum, tin/antimony, silver, or copper.

In one embodiment, the olefins 32 may be collected and sold for any number of known uses. In other embodiments, the olefins 32 are further processed in an olefin separation unit 40 and/or hydrogenation unit 50 (where the olefinic bonds are saturated with hydrogen gas 48, as described below). In other embodiments, the olefins 32 are selectively hydrogenated to increase the mono-olefin concentration. In other embodiments, esters 34 comprising heavier end glycerides and free fatty acids are separated or distilled as a bottoms product for further processing into various products. In certain embodiments, further processing may target the production of the following non-limiting examples: fatty acid methyl esters; biodiesel; 9DA esters, 9UDA esters, and/or 9DDA esters; 9DA, 9UDA, and/or 9DDA; alkali metal salts and alkaline earth metal salts of 9DA, 9UDA, and/or 9DDA; diacids, and/or diesters of the transesterified products; and mixtures thereof. In certain embodiments, further processing may target the production of C15-C18 fatty acids and/or esters. In other embodiments, further processing may target the production of diacids and/or diesters. In yet other embodiments, further processing may target the production of compounds having molecular weights greater than the molecular weights of stearic acid and/or linolenic acid.

As shown in FIG. 1, regarding the overhead olefins 32 from the separation unit 30, the olefins 32 may be further separated or distilled in the olefin separation unit 40 to separate the various compositions. The olefin separation unit 40 may comprise a number of distillation towers. In some embodiments, the various composition streams are separated using at least four distillation towers. In other embodiments, three towers or less are used to separate the olefin compositions.

In one embodiment, light end olefins 44 consisting of mainly C2-C9 compounds may be distilled into an overhead stream from the olefin separation unit 40. In certain embodiments, the light end olefins 44 are comprised of a majority of C3-C8 hydrocarbon compounds. In other embodiments, heavier olefins having higher carbon numbers may be separated overhead into the light end olefin stream 44 to assist in targeting a specific fuel composition. The light end olefins 44 may be recycled to the metathesis reactor 20, purged from the system for further processing and sold, or a combination of the two. In one embodiment, the light end olefins 44 may be partially purged from the system and partially recycled to the metathesis reactor 20. With regards to the other streams in the olefin separation unit 40, a heavier C16+, C18+, C20+, C22+, or C24+ compound stream may be separated out as an olefin bottoms stream 46. This olefin bottoms stream 46 may be purged or recycled to the metathesis reactor 20 for further processing, or a combination of the two. In another embodiment, a center-cut olefin stream 42 may be separated out of the olefin distillation unit for further processing. The center-cut olefins 42 may be designed to target a selected carbon number range for a specific fuel composition. As a non-limiting example, a C5-C15 distribution may be targeted for further processing into a naphtha-type jet fuel. Alternatively, a C8-C16 distribution may be targeted for further processing into a kerosene-type jet fuel. In another embodiment, a C8-C25 distribution may be targeted for further processing into a diesel fuel.

In some embodiments, processing steps may be conducted to maximize alpha olefin purity. In other embodiments, processing steps may be conducted to maximize C10 olefin purity. For example, C10+ olefins from the separation unit 30 or a particular olefin stream may be reacted with ethylene in the presence of a metathesis catalyst in a secondary metathesis reactor to improve the C10 olefin purity. In one embodiment, the metathesis catalyst is a rhenium oxide catalyst (e.g., rhenium oxide supported on alumina). In another embodiment, the metathesis is a tungsten oxide catalyst (e.g., tungsten oxide supported on silica). This metathesis reaction may be conducted in a fixed bed reactor. In some embodiments, the ethylene reagent can be recycled back to the secondary metathesis reactor. Lighter olefins (C4-C9) from the secondary metathesis reactor may be mixed with the main metathesis reactor olefins from the separation unit 30 for further processing.

In certain embodiments, the olefins 32 may be oligomerized to form poly-alpha-olefins (PAOs) or poly-internal-olefins (PIOs), mineral oil substitutes, and/or biodiesel fuel. The oligomerization reaction may take place after the distillation unit 30 or after the overhead olefin separation unit 40. In certain embodiments, byproducts from the oligomerization reactions may be recycled back to the metathesis reactor 20 for further processing.

In other embodiments, the olefins 32, light end olefins 44, or center-cut olefins 42 may be self-metathesized in the presence of a metathesis catalyst in a secondary metathesis reactor in order to produce heavier weight C14+, C16+, or C18+ olefin products. In one embodiment, the metathesis catalyst is a rhenium oxide catalyst (e.g., rhenium oxide supported on alumina). In another embodiment, the metathesis is a tungsten oxide catalyst (e.g., tungsten oxide supported on silica). This metathesis reaction may be conducted in a fixed bed reactor. The heavier weight C14+, C16+, or C18+ olefins may be used as surfactants or oil lubes. In some embodiments, the lighter olefin byproducts from the self-metathesis reaction may be recycled back to the secondary metathesis reactor or primary metathesis reactor 20 for further processing.

In certain embodiments, the olefins 32, center-cut olefins 42, light end olefins 44, or olefin bottoms 46 may be pretreated to remove potential catalyst poisons prior to the hydrogenation unit 50. Examples of potential feedstock pretreatments (such as adsorbants, alumina, or heat) for the olefin stream(s) are described above with regard to potential treatment of the natural oil 12.

As mentioned, in one embodiment, the olefins 32 from the separation unit 30 may be sent directly to the hydrogenation unit 50. In another embodiment, the center-cut olefins 42, light end olefins 44, or olefin bottoms 46 from the olefin separation unit 40 may be sent to the hydrogenation unit 50. Hydrogenation may be conducted according to any known method in the art for hydrogenating double bond-containing compounds such as the olefins 32, center-cut olefins 42, light end olefins 44, or olefin bottoms 46. In certain embodiments, in the hydrogenation unit 50, hydrogen gas 48 is reacted with the olefins 32, center-cut olefins 42, light end olefins 44, or olefin bottoms 46 in the presence of a hydrogenation catalyst to produce a hydrogenated product 52. Typical hydrogenation catalysts and reaction conditions are discussed above. During hydrogenation, the carbon-carbon double bond containing compounds in the olefins are hydrogenated to partially, selectively, or fully saturated compounds by the hydrogen gas 48.

In one embodiment, the resulting hydrogenated product 52 includes hydrocarbons with a distribution centered between approximately C10 and C12 hydrocarbons for naphtha- and kerosene-type jet fuel compositions. In another embodiment, the distribution is centered between approximately C16 and C18 for a diesel fuel composition.

In other embodiments, the olefins are selectively hydrogenated to decrease the presence of polyunsaturated olefins and increase the presence of monounsaturated olefins. The olefins 32 from the separation unit 30 may comprise polyolefins (e.g., dienes or trienes), with the amount of polyunsaturation depending on the inherent characteristics of the natural oil 12. Polyunsaturated olefins, such as dienes and trienes, may pose a number of problems for downstream processing and end-use over monounsaturated olefin compounds. Dienes and trienes may have oxidation rates that are 10-100 times those of monounsaturated olefins. These oxidation products would make some materials unsuitable for some applications such as advanced oilfield recovery. It therefore may prove beneficial to reduce the amount of polyunsaturation present in the olefins 32 from the separation unit 30. At the same time, olefins may be more valuable that paraffin compositions. Therefore, in some embodiments, the olefins 32, light end olefins 44, center-cut olefins 42, or olefin bottoms 46 are partially or selectively hydrogenated to remove the polyunsaturation and form monounsaturated olefins. The typical reaction conditions, such as temperature, pressure, time of reaction, and hydrogenation catalyst type, are described above with regard to partial or selective hydrogenation of the metathesis product 22.

Partially or Selectively hydrogenated olefin products 52 may be useful for the preparation of surfactants/surfactant precursors including but not limited to linear alkyl benzene. In certain embodiments, the partially or the selectively hydrogenated product 52 may be useful for but not limited to advanced oilfield recovery or drilling fluids.

In certain embodiments, in the diene selective hydrogenation, the conversion rate from polyunsaturated olefins to paraffins and monounsaturated olefins may be at least 50%, at least 75%, at least 85%, at least 95%, or at least 98%. The selectivity towards monounsaturated olefins instead of paraffin is at least 90%, at least 95%, at least 99%, or at least 99.5%.

In certain embodiments, after full, partial, or selective hydrogenation, the hydrogenation catalyst may be removed from the hydrogenated product 52 using known techniques in the art, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the product directly or it may be applied to the filter. Representative non-limiting examples of filtering aids include diatomaceous earth, silica, alumina, and carbon. Typically, the filtering aid is used in an amount of about 10 weight % or less, for example, about 5 weight % or less or about 1 weight % or less. Other filtering techniques and filtering aids also may be employed to remove the used hydrogenation catalyst. In other embodiments the hydrogenation catalyst is removed using centrifugation followed by decantation of the product.

In certain embodiments, based upon the quality of the hydrogenated product 52 produced in the hydrogenation unit 50, it may be preferable to isomerize the olefin hydrogenated product 52 to assist in targeting of desired product properties such as flash point, freeze point, energy density, cetane number, or end point distillation temperature, among other parameters. Isomerization reactions are well-known in the art, as described in U.S. Pat. Nos. 3,150,205; 4,210,771; 5,095,169; and 6,214,764, herein incorporated by reference in their entireties. In one embodiment, the isomerization reaction at this stage may also crack some of the C15+ compounds remaining, which may further assist in producing a fuel composition having compounds within the desired carbon number range, such as 5 to 16 for a jet fuel composition.

In certain embodiments, the isomerization may occur concurrently with the hydrogenation step in the hydrogenation unit 50, thereby targeting a desired product. In other embodiments, the isomerization step may occur before the hydrogenation step (i.e., the olefins 32 or center-cut olefins 42 may be isomerized before the hydrogenation unit 50). In yet other embodiments, it is possible that the isomerization step may be avoided or reduced in scope based upon the selection of low-molecular-weight olefin(s) 14 and/or mid-weight olefin(s) 15 used in the metathesis reaction.

In certain embodiments, the hydrogenated product 52 is a partially or selectively hydrogenated product stream that comprises approximately 15-25 weight % C7, approximately <5 weight % C8, approximately 20-40 weight % C9, approximately 20-40 weight % C10, approximately <5 weight % C11, approximately 15-25 weight % C12, approximately <5 weight % C13, approximately <5 weight % C14, approximately <5 weight % C15, approximately <1 weight % C16, approximately <1 weight % C17, and approximately <1 weight % C18+.

As shown in FIG. 1, the hydrogenated product 52 may be further processed in a separation unit 60, removing any remaining byproducts from the hydrogenated product 52, such as hydrogen gas, water, light end C2-C9 hydrocarbons, or C15+ hydrocarbons, thereby producing a targeted composition. The separation unit 60 may comprise a number of distillation towers. In some embodiments, the various composition streams are separated using at least four distillation towers. In other embodiments, three towers or less are used.

In one embodiment, the hydrogenated product 52 may be separated into various product cuts, such as a C9-C15 product 64, a light-ends C2-C9 fraction 62, and/or a C15+ heavy-ends fraction 66. Distillation may be used to separate the fractions. Alternatively, in other embodiments, the heavy ends fraction 66 can be separated from the C9-C15 product 64 by cooling the hydrogenated product 52 to approximately −40° C., −47° C., or −65° C. and then removing the solid, heavy ends fraction 66 by techniques known in the art such as filtration, decantation, or centrifugation.

With regard to the esters 34 from the distillation unit 30, in certain embodiments, the esters 34 may be entirely withdrawn as an ester product stream 36 and processed further or sold for its own value, as shown in FIG. 1. As a non-limiting example, the esters 34 may comprise various triglycerides that could be used as a lubricant. Based upon the quality of separation between olefins and esters, the esters 34 may comprise some heavier olefin components carried with the triglycerides. In other embodiments, the esters 34 may be further processed in a biorefinery or another chemical or fuel processing unit known in the art, thereby producing various products such as biodiesel or specialty chemicals that have higher value than that of the triglycerides, for example. Alternatively, in certain embodiments, the esters 34 may be partially withdrawn from the system and sold, with the remainder further processed in the biorefinery or another chemical or fuel processing unit known in the art.

In some embodiments, the esters 34 may be pre-treated to remove potential catalyst poisons prior to further processing. Examples of potential feedstock pretreatments (such as adsorbants, alumina, or heat) for the esters 34 are described above with regard to potential treatment of the natural oil 12.

In certain embodiments, the esters 34 may be selectively hydrogenated to decrease the presence of polyunsaturated esters and increase the presence of monounsaturated esters. Typical reaction conditions, such as temperature, pressure, time of reaction, and hydrogenation catalyst type, are described above with regard to selective hydrogenation of the metathesis product 22.

In certain embodiments, in the diene selective hydrogenation, the conversion rate from polyunsaturated esters to saturated and monounsaturated esters may be at least 50%, at least 75%, at least 85%, at least 95%, or at least 98%. The selectivity towards monounsaturated esters instead of saturated esters is at least 90%, at least 95%, at least 99%, or at least 99.5%.

In certain embodiments, the ester stream 34 (which has been selectively hydrogenated in some embodiments) is sent to a transesterification unit 70. Within the transesterification unit 70, the esters 34 are reacted with at least one alcohol 38 in the presence of a transesterification catalyst. In certain embodiments, the alcohol comprises methanol and/or ethanol. In another embodiment, the alcohol 38 comprises glycerol (and the transesterification reaction is a glycerolysis reaction). In one embodiment, the transesterification reaction is conducted at approximately 60-70° C. and approximately 1 atm. In certain embodiments, the transesterification catalyst is a homogeneous sodium methoxide catalyst. Varying amounts of catalyst may be used in the reaction, and, in certain embodiments, the transesterification catalyst is present in the amount of approximately 0.5-1.0 weight % of the esters 34.

In certain embodiments, the transesterification reaction may produce a transesterified product 72 comprising monomer terminal olefin esters having the following structure:

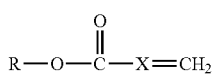

where X is a C3-C18 saturated or unsaturated alkyl chain, and R is an alkyl group. In some embodiments, R is methyl.

The transesterification reaction may produce transesterified products 72 including saturated and/or unsaturated monomer fatty acid methyl esters ("FAME"), glycerin, methanol, and/or free fatty acids. In certain embodiments, the transesterified products 72, or a fraction thereof, may comprise a source for biodiesel. In certain embodiments, the transesterified products 72 comprise C10-C15 or C11-C14 esters. In certain embodiments, the transesterified products 72 comprise 9DA esters, 9UDA esters, and/or 9DDA esters. Non-limiting examples of 9DA esters, 9UDA esters and 9DDA esters include methyl 9-decenoate ("9-DAME"), methyl 9-undecenoate ("9-UDAME"), and methyl 9-dodecenoate ("9-DDAME"), respectively. As a non-limiting example, in a transesterification reaction, a 9DA moiety of a metathesized glyceride is removed from the glycerol backbone to form a 9DA ester.

As discussed above, the types of transesterified products formed are based upon the reactants entering the metathesis reactor 20. In one particular embodiment, C12 methyl esters (9-DDAME) are produced downstream of the metathesis reaction between 3-hexene and a natural oil.

In another embodiment, a glycerin alcohol may be used in the reaction with a glyceride stream. This reaction may produce monoglycerides and/or diglycerides.

In certain embodiments, the transesterified products 72 from the transesterification unit 70 can be sent to a liquid-liquid separation unit, wherein the transesterified products 72 (i.e., FAME, free fatty acids, and/or alcohols) are separated from glycerin. Additionally, in certain embodiments, the glycerin byproduct stream may be further processed in a secondary separation unit, wherein the glycerin is removed and any remaining alcohols are recycled back to the transesterification unit 70 for further processing.

In certain embodiments, the transesterified products 72 can be sent to a hydrogenation unit for selective hydrogenation, wherein the concentration of monounsaturated esters is increased by diene-selective hydrogenation. Typical reaction conditions, such as temperature, pressure, time of reaction, and hydrogenation catalyst type, are described above with regard to selective hydrogenation of the metathesis product 22.

In certain embodiments, in the diene selective hydrogenation, the conversion rate from the transesterified polyunsaturated esters to saturated and monounsaturated transesterified esters may be at least 50%, at least 75%, at least 85%, at least 95%, or at least 98%. The selectivity towards the monounsaturated esters instead of saturated esters is at least 90%, at least 95%, at least 99%, or at least 99.5%.

In one embodiment, the transesterified products 72 are further processed in a water-washing unit. In this unit, the transesterified products undergo a liquid-liquid extraction when washed with water. Excess alcohol, water, and glycerin are removed from the transesterified products 72. In another embodiment, the water-washing step is followed by a drying unit in which excess water is further removed from the desired mixture of esters (i.e., specialty chemicals). Such specialty chemicals include non-limiting examples such as 9DA, 9UDA, and/or 9DDA, alkali metal salts and alkaline earth metal salts of the preceding, individually or in combinations thereof.

In one embodiment, the monomer specialty chemical (e.g., 9DA) may be further processed in an oligomerization reaction to form a lactone, which may serve as a precursor to a surfactant.

In certain embodiments, the transesterifed products 72 from the transesterification unit 70 or specialty chemicals from the water-washing unit or drying unit are sent to an ester distillation column 80 for further separation of various individual or groups of compounds, as shown in FIG. 1. This separation may include, but is not limited to, the separation of 9DA esters, 9UDA esters, and/or 9DDA esters. In one embodiment, the 9DA ester 82 may be distilled or individually separated from the remaining mixture 84 of transesterified products or specialty chemicals. In certain process conditions, the 9DA ester 82 should be the lightest component in the transesterified product or specialty chemical stream, and come out at the top of the ester distillation column 80. In another embodiment, the remaining mixture 84, or heavier components, of the transesterified products or specialty chemicals may be separated off the bottom end of the column. In certain embodiments, this bottoms stream 84 may potentially be sold as biodiesel.

The 9DA esters, 9UDA esters, and/or 9DDA esters may be further processed after the distillation step in the ester distillation column. In one embodiment, under known operating conditions, the 9DA ester, 9UDA ester, and/or 9DDA ester may then undergo a hydrolysis reaction with water to form 9DA, 9UDA, and/or 9DDA, alkali metal salts and alkaline earth metal salts of the preceding, individually or in combinations thereof.

In certain embodiments, the monomer fatty acid esters from the transesterified products 72 may be reacted with each other to form other specialty chemicals such as dimers.

In other embodiments, specific ester products, such as 9DDA methyl ester, may be enriched through subsequent processing and reaction steps of the transesterified products. In one embodiment, a C10 methyl ester stream may be separated from heavier C12+ methyl esters. The C10 methyl ester stream may then be reacted with 1-butene in the presence of a metathesis catalyst to form C12 methyl esters and ethylene. The ethylene may be separated from the methyl esters and the C10 and C12 methyl esters may be removed or returned to an ester distillation column for further processing.

In certain embodiments, the monomer fatty acids and/or monomer fatty acid esters from the transesterified products 72 are isomerized to form isomerized monomer fatty acids and/or isomerized monomer fatty acid esters. The isomerization of the fatty acids and/or fatty acid esters from the transesterified products 72 may be conducted at an elevated temperature (i.e., greater than 25° C.). In certain embodiments, the temperature of the heat treatment for the isomerization reaction is greater than 100° C., greater than 150° C., or greater than 200° C. In other embodiments, the temperature is between 100° C.-300° C., between 150-250° C., or about 200° C. In some embodiments, the heat treatment step is conducted in the presence of an isomerization catalyst. In one particular embodiment, the isomerization catalyst is $(PCy_3)_2(Cl)(H)Ru(CO)$, where "Cy" represents a cyclohexyl group.

In certain embodiments, the monomer fatty acids and/or monomer fatty acid esters that undergo the isomerization reaction are selected from the group consisting of: 9DA, 9DA esters, 9UDA, 9UDA esters, 9DDA, and 9DDA esters. The isomerization of the fatty acids and/or fatty acid esters may produce isomerized monomer fatty acids and/or isomerized monomer fatty acid esters selected from the group consisting of isomerized 9DA, isomerized 9DA esters, isomerized 9UDA, isomerized 9UDA esters, isomerized 9DDA, and isomerized 9DDA esters.

Isomerizing the monomer fatty acids and/or monomer fatty acid esters may improve various performance properties. For example, the isomerized product composition may have an observed broadening of the freezing and melting points, which may allow for transportation of the isomerized fatty acid/ester product composition at higher concentrations of the monomer fatty acids and/or monomer fatty acid esters without incurring shipping problems.

Isomerized monomer fatty acids and/or isomerized monomer fatty acid esters may be used in a variety of different commercial applications, including, but not limited to: lubricants, waxes, films, paints, paint strippers, coatings, plasticizers, resins, binders, solvents, polyols, soil stabilization, chemical grouting, oilfield drilling fluids, crop protection products, surfactants, intermediates, and adhesives.

In certain embodiments, the transesterified product 72 comprises terminal olefin esters and is cross-metathesized with an internal olefin in the presence of a metathesis catalyst to produce a dibasic acid and/or dibasic ester, as well as an olefin byproduct. As mentioned above, the transesterified product 72 may comprise terminal olefins having the following structure:

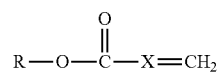

where X is a C3-C18 saturated or unsaturated alkyl chain, and R is an alkyl group or hydrogen.

In certain embodiments, the terminal olefin-internal olefin cross-metathesis reaction is conducted at a weight ratio between 1:99 (terminal to internal) and 99:1 (terminal to internal). In other embodiments, the weight ratio of the terminal and internal olefin is between 1:5 and 5:1. In yet other embodiments, the weight ratio between the terminal and internal olefin is between 1:2 and 2:1. In one particular embodiment, the weight ratio between the terminal and internal olefin is approximately 1:1.

In certain embodiments, the terminal olefin is selected from the group consisting of: 4-pentenoic acid ester, 5-hexenoic acid ester, 6-heptenoic acid ester, 7-octenoic acid ester, 8-nonenoic acid ester, 9-decenoic acid ester, 10-undecenoic acid ester, 11-dodecenoic acid ester, 12-tridecenoic acid ester, 13-tetradecenoic acid ester, 14-pentadecenoic acid ester, 15-hexadecenoic acid ester, 16-heptadecenoic acid ester, 17-octadecenoic acid ester, acids thereof, and mixtures thereof. In one particular embodiment, the terminal olefin is 9-decenoic acid ester.

In certain embodiments, the terminal olefin is cross-metathesized with an internal olefin selected from the group consisting of: pentenoic acid esters, hexenoic acid esters, heptenoic acid esters, octenoic acid esters, nonenoic acid esters, decenoic acid esters, undecenoic acid esters, dodecenoic acid esters, tridecenoic acid esters, tetradecenoic acid esters, pentadecenoic acid esters, hexadecenoic acid esters, heptadecenoic acid esters, octadecenoic acid esters, acids thereof, and mixtures thereof. In one particular embodiment, the internal olefin is 9-undecenoic acid ester. In another particular embodiment, the internal olefin is 9-dodecenoic acid ester.

In some embodiments, the internal olefin is formed by reacting a portion of the terminal olefin ester derived from the transesterified product 72 with a low-molecular-weight internal olefin or mid-weight internal olefin in the presence of a metathesis catalyst. In certain embodiments, the low-molecular-weight internal olefin is selected from the group consisting of: 2-butene, 2-pentene, 2-hexene, 3-hexene, 2-heptene, 3-heptene, 2-octene, 3-octene, 4-octene, 2-nonene, 3-nonene, 4-nonene, and mixtures thereof. In one particular embodiment, the low-molecular-weight internal olefin is 2-butene. In another particular embodiment, the low-molecular-weight internal olefin is 3-hexene.

In certain embodiments, at least 70 wt %, 80 wt %, or 90 wt % dibasic ester and/or dibasic acid is formed from the cross-metathesis reaction of a terminal olefin and an internal olefin in the presence of less than 150 ppm, 100 ppm, 50 ppm, 25 ppm, or 10 ppm catalyst. A comparable self-metathesis reaction with terminal olefins (such as 9-decenoic acid ester) under similar reaction conditions may require more catalyst (e.g., more than 150 ppm, or more than 500 ppm) to achieve similar yields of dibasic esters and/or dibasic acids (potentially due to the formation of the ethylene byproduct).

In certain embodiments, the dibasic ester and/or dibasic acid yield is improved by separating the olefin byproduct formed in the cross-metathesis reaction from the metathesis product while the reaction between the terminal olefin and internal olefin is ongoing. In other embodiments, the dibasic ester and/or dibasic acid yield is improved by sparging the metathesis products in the metathesis reactor with a chemically inert gas (e.g., nitrogen, argon, or helium) to ventilate dissolved gases/byproducts (e.g., olefin byproducts) in the metathesis product.

In certain embodiments, the cross-metathesis reaction of the terminal olefin and internal olefin produces a dibasic ester comprising the following structure:

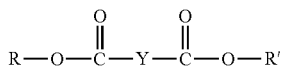

wherein R and R' are independently alkyl or aryl groups, and Y is an olefin comprising between 6 and 36 carbon atoms. In some embodiments, the cross-metathesis reaction forms a C21-C24 dibasic ester. In one embodiment, the cross-metathesis reaction forms a dibasic ester, where R and R' are methyl and Y is 8-hexadecene (i.e., the dibasic ester formed from the cross-metathesis reaction of a terminal olefin and an internal olefin is dimethyl 9-octadecenedioate). In some embodiments, these dibasic esters would be selectively hydrogenated to increase the concentration of monounsaturated dibasic esters.

In some embodiments, the dibasic ester derived from the transesterified product 72 may further undergo a hydrolysis reaction with water to form a dibasic acid having the following structure:

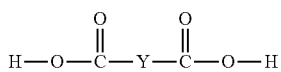

wherein Y is an olefin comprising between 6 and 36 carbon atoms. In one embodiment, Y is 8-hexadecene (i.e., the dibasic acid is 9-octadecene dioic acid).

Following hydrolysis, in some embodiments, the product stream may be sent to a flash column or decanter to remove methanol and water from the diacid.

In other embodiments, the dibasic acid and/or dibasic ester is isomerized to form an isomerized dibasic acid and/or isomerized dibasic ester. The isomerization of the dibasic acid and/or dibasic ester may be conducted at an elevated temperature (i.e., greater than 25° C.). In certain embodiments, the temperature of the heat treatment for the isomerization reaction is greater than 100° C., greater than 150° C., or greater than 200° C. In other embodiments, the temperature is between 100° C.-300° C., between 150-250° C., or about 200° C. In some embodiments, the heat treatment step is conducted in the presence of an isomerization catalyst. In one particular embodiment, the isomerization catalyst is (PCy$_3$)$_2$(Cl)(H)Ru(CO), where "Cy" represents a cyclohexyl group.

In certain embodiments, the isomerized dibasic acid and/or isomerized dibasic ester comprises compounds selected from the group consisting of: isomerized dimethyl 9-octadecenedioate or isomerized 9-octadecene dioic acid.

In certain embodiments, the isomerized dibasic acid and/or isomerized dibasic ester is self-metathesized or cross-metathesized with a low-molecular-weight olefin or mid-weight olefin. Typical metathesis reaction conditions and catalysts are discussed in greater detail below. In one embodiment, the isomerized dibasic acid and/or isomerized dibasic ester is self-metathesized in the presence of approximately 10 ppm, 20 ppm, 40 ppm, 50 ppm, 80 ppm, 100 ppm, 120 ppm, or greater than 150 ppm metathesis catalyst.

In certain embodiments, the isomerized fatty acid, isomerized fatty acid ester, dibasic acid, dibasic ester, isomerized dibasic acid, and/or isomerized dibasic ester is fully hydrogenated. Typical hydrogenation reaction conditions and catalysts are discussed above. In one particular embodiment, the hydrogenation reaction is conducted in the presence of a nickel based catalyst at approximately 150° C. and 150 psig. In another embodiment, the hydrogenation reaction is conducted in the presence of a nickel based catalyst at approximately 150° C. and 100 psig. In certain embodiments, these dibasic materials are selectively hydrogenated to increase the concentration of monounsaturated compounds.

As noted, the self-metathesis of the natural oil, cross-metathesis between the natural oil and low-molecular-weight olefin or mid-weight olefin, or cross-metathesis between a terminal olefin and internal olefin occurs in the presence of a metathesis catalyst. As stated previously, the term "metathesis catalyst" includes any catalyst or catalyst system that catalyzes a metathesis reaction. Any known or future-developed metathesis catalyst may be used, individually or in combination with one or more additional catalysts. Non-limiting exemplary metathesis catalysts and process conditions are described in PCT/US2008/009635, pp. 18-47, incorporated by reference herein. A number of the metathesis catalysts as shown are manufactured by Materia, Inc. (Pasadena, Calif.).

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene.

In other embodiments, the metathesis catalyst is not dissolved in a solvent prior to conducting the metathesis reaction. The catalyst, instead, may be slurried with the natural oil 12, where the natural oil 12 is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil 12 (e.g., as an auger feed).

The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa).

While the invention as described may have modifications and alternative forms, various embodiments thereof have been described in detail. It should be understood, however, that the description herein of these various embodiments is not intended to limit the invention, but on the contrary, the intention is to cover all modifications, equivalents, and alternatives falling within the spirit and scope of the invention as defined by the claims. Further, while the invention will also be described with reference to the following non-limiting examples, it will be understood, of course, that the invention is not limited thereto since modifications may be made by those skilled in the art, particularly in light of the foregoing teachings.

EXAMPLES

Example 1

Selective Hydrogenation of C9/C10 Olefins with PRICAT CU 50/8 P

In a 600 mL Parr reactor, 300 g C9/C10 Feedstock (88.0% C9, 10.5% C10) and 1.52 g PRICAT CU 50/8 P (0.5 wt %) were purged with $N_2$, then $H_2$, for 15 minutes each, then reacted at 180° C., 100 psig $H_2$, and 900 rpm stirring with a gas dispersion impeller. The $H_2$ pressure was monitored and the reactor was refilled to 100 psig when it decreased to 50 psig. Samples of the reaction mixture were taken at 30, 60, 120, 180, and 240 minutes. The reaction was monitored using GC for both the disappearance of polyenes and the formation of paraffin and monounsaturated olefins. The reaction proceeded to 95% conversion with 92% selectivity to the monounsaturated olefin products (C9:1, C10:1) in 2 hours. The reaction mixture was gravity filtered and the clear product recovered.

Example 2

Selective Hydrogenation of C9/C10 Olefins with PRICAT 9908

In a 600 mL Parr reactor, 300 g C9/C10 Feedstock (88.0% C9, 10.5% C10) and 0.74 g PRICAT 9908 (0.25 wt %, triglycerides removed before reaction) were purged with $N_2$, then $H_2$, for 15 minutes each, then reacted at 150° C., 100 psig $H_2$, and 900 rpm stirring with a gas dispersion impeller. The $H_2$ pressure was monitored and the reactor was refilled to 100 psig when it decreased to 50 psig. Samples of the reaction mixture were taken at 30, 60, 120, 180, and 240 minutes. The reaction was monitored using GC for both the disappearance of polyenes and the formation of paraffin and monounsaturated olefins. The reaction proceeded to 85% conversion with 95% selectivity to the monounsaturated olefins (C9:1, C10:1) in 30 min. The reaction mixture was gravity filtered and the clear product recovered.

Example 3

Selective Hydrogenation of Purified C12 Olefins with PRICAT 9908

In a 600 mL Parr reactor, 300 g C12 Feedstock (purified by alumina column and molecular sieves, 99.6% C12) and 0.31 g PRICAT 9908 (0.1 wt %, triglycerides removed before reaction) were purged with $N_2$, then $H_2$, for 15 minutes each, then reacted at 180° C., 100 psig $H_2$, and 1000 rpm stirring with a gas dispersion impeller. The $H_2$ pressure was monitored, and the reactor was refilled to 100 psig when it decreased to 50 psig. Samples of the reaction mixture were taken at 15, 30, 45, 60, and 75 minutes. The disappearance of C12:2 diene and formation of C12:0 paraffin and C12:1 monoene were monitored using GC. The reaction proceeded to 96.5% conversion with 98.4% selectivity to C12:1 in 30 min. The reaction mixture was gravity filtered, and the clear product was recovered.

Example 4

Selective Hydrogenation of Purified C12 Olefins with PRICAT 9908 and PRICAT CU 50/8 P In a 600 mL Parr reactor, 300 g C12 Feedstock (purified by alumina column and molecular sieves, 99.6% C12), 0.30 g PRICAT 9908 (0.1 wt %), and 0.02 g PRICAT CU 50/8 P (0.005 wt %) were purged with $N_2$, then $H_2$, for 15 minutes each. This was then reacted at 180° C., 100 psig $H_2$, and 1000 rpm stirring with a gas dispersion impeller. The $H_2$ pressure was monitored, and the reactor was refilled to 100 psig when it decreased to 50 psig. Samples of the reaction were taken at 15, 30, 45, and 60 minutes. The disappearance of C12:2 diene and formation of C12:0 paraffin and C12:1 monoene were monitored using GC. The reaction proceeded to 94.3% conversion with 97.6% selectivity to C12:1 in 30 min. The reaction mixture was gravity filtered, and the clear product was recovered.

Example 5

Selective Hydrogenation of Purified C12 Olefins with PRICAT CU 50/8 P and PRICAT 9908

In a 600 mL Parr reactor, 300 g C12 Feedstock (purified by alumina column and molecular sieves, 99.6% C12), 0.90 g PRICAT CU 50/8P (0.30 wt %), and 0.05 g PRICAT 9908 (0.015 wt %) were purged with $N_2$, then $H_2$, for 15 minutes each, then reacted at 180° C., 100 psig $H_2$, and 100 rpm stirring with a gas dispersion impeller. The $H_2$ pressure was monitored: the reactor was refilled to 100 psig when it decreased to 50 psig. Samples of the reaction mixture were taken at 15, 30, 45, 60, and 75 minutes. The disappearance of C12:2 diene and formation of C12:0 paraffin and C12:1 monoene were monitored using GC. The reaction proceeded to 96.7% conversion with 92.9% selectivity to C12:1 in 30 min. The reaction mixture was gravity filtered, and the clear product was recovered.

Example 6

Selective Hydrogenation of Purified C12 Olefins with PRICAT CU 50/8 P

In a 600 mL Parr reactor, 300 g C12 Feedstock (purified by alumina column and molecular sieves, 99.6% C12) and 0.90 g PRICAT CU 50/8 P (0.30 wt %) were purged with $N_2$, then $H_2$, for 15 minutes each, then reacted at 180° C., 100 psig $H_2$, and 100 rpm stirring with a gas dispersion impeller. The $H_2$ pressure was monitored: the reactor was refilled to 100 psig when it decreased to 50 psig. Samples of the reaction mixture were taken at 15, 30, 45, and 60 minutes. The disappearance of C12:2 diene and formation of C12:0 paraffin and C12:1 monoene were monitored using GC. The reaction proceeded to 98.6% conversion with 99.7% selectivity to C12:1 in 30 min. The reaction mixture was gravity filtered, and the clear product was recovered.

Example 7

Selective Hydrogenation of Purified C12 Olefins with PRICAT CU 50/8 P

In a 600 mL Parr reactor, 300 g C12 Feedstock (purified by alumina column and molecular sieves, 99.6% C12) and 0.90 g PRICAT CU 60/35 P (0.30 wt %) were purged with $N_2$, then $H_2$, for 15 minutes each, then reacted at 180° C., 100 psig $H_2$, and 100 rpm stirring with a gas dispersion impeller. The $H_2$ pressure was monitored, and the reactor was refilled to 100 psig when it decreased to 50 psig. Samples of the reaction mixture were taken at 15, 30, 45, 60, and 90 minutes. The disappearance of C12:2 diene and formation of C12:0 paraffin and C12:1 monoene were monitored using GC. The reaction proceeded to 73.3% conversion with 99.4% selectivity to C12:1 in 90 min. The reaction mixture was gravity filtered, and the clear product was recovered.

Example 8

Purification of C12/C13 Olefins by Alumina Column

To purify the sample, the C12/C13 Feedstock was passed through an activated alumina column, then dried over 4 Å molecular sieves overnight, under a $N_2$ atmosphere. The peroxide value was reduced to 1.90 meq/mg, and the water content, as determined by Karl Fisher titration, was reduced to 49.77 ppm.

Example 9

Selective Hydrogenation of Purified C12/C13 Olefins with PRICAT CU 9908

In a 600 mL Parr reactor, 300 g C12/C13 Feedstock (purified by alumina column and molecular sieves, 93.4% C12, 4.4% C13) and 0.30 g PRICAT 9908 (0.10 wt %, triglycerides removed before reaction) were purged with $N_2$, then $H_2$, for 15 minutes each, then reacted at 150° C., 100 psig $H_2$, and 1000 rpm stirring with a gas dispersion impeller. The $H_2$ pressure was monitored: the reactor was refilled to 100 psig when it decreased to 50 psig. Samples of the reaction mixture were taken at 30, 60, 90, and 120 minutes. The disappearance of diene (C12:2 and C13:2) and the formation of monoene (C12:1 and C13:1) and paraffin (C12:0 and C13:0) were monitored by GC. The reaction proceeded to 78.3% conversion with 94.0% selectivity to the monounsaturated olefin products in 90 min. The reaction mixture was gravity filtered and the clear product recovered.

Example 10

Selective Hydrogenation of Purified C12/C13 Olefins with PRICAT CU 50/8 P

In a 600 mL Parr reactor, 300 g C12/C13 Feedstock (purified by alumina column and molecular sieves, 93.4% C12, 4.4% C13) and 0.90 g PRICAT CU 50/8 P (0.30 wt %) were purged with $N_2$, then $H_2$, for 15 minutes each, then reacted at 180° C., 100 psig $H_2$, and 1000 rpm stirring with a gas dispersion impeller. The $H_2$ pressure was monitored: the reactor was refilled to 100 psig when it decreased to 50 psig. Samples of the reaction mixture were taken at 30 and 45 minutes. The disappearance of diene (C12:2 and C13:2) and the formation of monoene (C12:1 and C13:1) and paraffin (C12:0 and C13:0) were monitored using GC. The reaction proceeded to 97.7% conversion with 97.2% selectivity to the monounsaturated olefin products in 30 min. The reaction mixture was gravity filtered and the clear product recovered.

Example 11

Selective Hydrogenation of Purified C12/C13 Olefins with PRICAT CU 50/8 P

In a 600 mL Parr reactor, 300 g C12/C13 Feedstock (purified by alumina column and molecular sieves, 93.4% C12, 4.4% C13) and 1.33 g once reacted PRICAT CU 50/8 P (0.44 wt %) were purged with $N_2$, then $H_2$, for 15 minutes each, then reacted at 180° C., 100 psig $H_2$, and 1000 rpm stirring with a gas dispersion impeller. The $H_2$ pressure was monitored: the reactor was refilled to 100 psig when it decreased to 50 psig. Samples of the reaction mixture were taken at 30 and 60 minutes. The disappearance of diene (C12:2 and C13:2) and the formation of monoene (C12:1 and C13:1) and paraffin (C12:0 and C13:0) were monitored using GC. The reaction proceeded to 93.2% conversion with 98.2% selectivity to the monounsaturated olefin products in 60 min. The reaction mixture was gravity filtered and the clear product was recovered.

Example 12

Selective Hydrogenation of Purified C12/C13 Olefins with Twice Recycled PRICAT CU 50/8 P In a 600 mL Parr reactor, 300 g C12/C13 Feedstock (purified by alumina column and molecular sieves, 93.4% C12, 4.4% C13) and 1.05 g twice reacted PRICAT CU 50/8 P (0.35 wt %) were purged with $N_2$, then $H_2$, for 15 minutes each, then reacted at 180° C., 100 psig $H_2$, and 1000 rpm stirring with a gas dispersion impeller. The $H_2$ pressure was monitored: the reactor was refilled to 100 psig when it decreased to 50 psig. Samples of the reaction mixture were taken at 30 and 60 minutes. The disappearance of diene (C12:2 and C13:2) and the formation of monoene (C12:1 and C13:1) and paraffin (C12:0 and C13:0) were monitored using GC. The reaction proceeded to 94.4% conversion with 99.5% selectivity to the monounsaturated olefin products in 60 min. The reaction mixture was gravity filtered and the clear product recovered.

Example 13

Selective Hydrogenation of C13 Olefins with PRICAT CU 50/8 P

In a 600 mL Parr reactor, 300 g C13 Feedstock (90.6% C13) and 3.10 g PRICAT CU 50/8 P (1.0 wt %) were purged with $N_2$, then $H_2$, for 15 minutes each, then reacted at 180° C., 100 psig $H_2$, and 1000 rpm stirring with a gas dispersion impeller. The $H_2$ pressure was monitored: the reactor was refilled to 100 psig when it decreased to 50 psig. Samples of the reaction mixture were obtained at 30, 60, 90, 120, 180, and 240 minutes. The reaction was monitored using GC for both the disappearance of C13:2 olefins and the formation of C13:0 and C13:1 olefins. The reaction proceeded to 27.3% conversion with 99.6% selectivity to C13:1 in 2 hours. The reaction was gravity filtered and the clear product recovered.

Example 14

Selective Hydrogenation of Purified C13 Olefins with PRICAT CU 50/8 P

In a 600 mL Parr reactor, 300 g C13 Feedstock (purified by alumina column and molecular sieves, 90.6% C13) and 3.04 g PRICAT CU 50/8 P (1.0 wt %) were purged with $N_2$, then $H_2$, for 15 minutes each, then reacted at 180° C., 100 psig $H_2$, and 1000 rpm stirring with a gas dispersion impeller. The $H_2$ pressure was monitored: the reactor was refilled to 100 psig when it decreased to 50 psig. Samples of the reaction mixture were taken at 30, 60, 90, 120, 150, 180, and 210 minutes. The reaction was monitored for both the disappearance of the C13:2 olefins and the formation of C13:0 and C13:1 olefins using GC. The reaction proceeded to 96.8% conversion with 91.9% selectivity to C13:1 in 2 hours. The reaction was gravity filtered and the clear product recovered.

Example 15

Selective Hydrogenation of Purified C13 Olefins with PRICAT 9908

In a 600 mL Parr reactor, 300 g C13 Feedstock (purified by alumina column and molecular sieves, 90.6% C13) and 0.29 g PRICAT 9908 (0.1 wt %, triglycerides removed before reaction) were purged with $N_2$, then $H_2$, for 15 minutes each. These were then reacted at 150° C., 100 psig $H_2$, and 1000 rpm stirring with a gas dispersion impeller. The $H_2$ pressure was monitored, and the reactor was refilled to 100 psig when it decreased to 50 psig. Samples of the reaction mixture were taken at 30, 60, and 90 minutes. The reaction was monitored for both the disappearance of the C13:2 olefins and the formation of C13:0 and C13:1 olefins using GC. The reaction proceeded to 98.6% conversion with 94.9% selectivity to the monounsaturated olefin products in 60 min. The reaction was gravity filtered and the clear product recovered.

Example 16

Selective Hydrogenation of Purified C15-C18 Olefins with PRICAT CU 50/8 P

In a 600 mL Parr reactor, 300 g C15-18 Feedstock (purified by alumina column and molecular sieves, 50.6% C15, 3.8% C16, 1.4% C17, 23.6% C18) and 0.30 g PRICAT CU 50/8 P (0.1 wt %) were purged with $N_2$, then $H_2$, for 15 minutes each. These were then reacted at 150° C., 100 psig $H_2$, and 1000 rpm stirring with a gas dispersion impeller. The $H_2$ pressure was monitored, and the reactor was refilled to 100 psig when it decreased to 50 psig. Samples of the reaction mixture were taken at 30, 60, 90, 120, 150, and 180 minutes. The reaction was monitored for both the disappearance of dienes (C15:2, C16:2, C17:2, and C18:2), and for the formation of saturates (C15:0, C16:0, C17:0, and C18:0) and monoenes (C15:1, C16:1, C17:1, and C18:1) using GC. The reaction proceeded to 86.7% conversion with 99.5% selectivity to the monounsaturated olefin products in 90 min. The reaction was gravity filtered and the clear product recovered.

Example 17

Selective Hydrogenation of Purified C18 Olefins with PRICAT CU 50/8 P

In a 600 mL Parr reactor, 300 g C18 Feedstock (purified by alumina column and molecular sieves, 98.7% C18) and 0.31 g PRICAT CU 50/8 P (0.1 wt %) were purged with $N_2$, then $H_2$, for 15 minutes each. These were then reacted at 180° C., 100 psig $H_2$, and 100 rpm stirring with a gas dispersion impeller. The $H_2$ pressure was monitored, and the reactor refilled to 100 psig when it decreased to 50 psig. Samples of the reaction were taken at 15, 30, and 45 minutes. The reaction was monitored for both the disappearance of C18:2 olefins and for the formation of C18:0 and C18:1 olefins using GC. The reaction proceeded to 93.8% conversion with 99.4% selectivity to C18:1 in 45 min. This was over a period of 45 minutes. The reaction was gravity filtered, and the clear product was recovered.

Example 18

Selective Hydrogenation of Purified C18 Olefins with PRICAT 9908

In a 600 mL Parr reactor, 300 g C18 Feedstock (purified by alumina column and molecular sieves, 98.7% C18) and 0.07 g PRICAT 9908 (0.02 wt %, triglycerides removed before reaction) were purged with $N_2$, then $H_2$, for 15 minutes each. This was then reacted at 160° C., 100 psig $H_2$, and 1000 rpm stirring with a gas dispersion impeller. The $H_2$ pressure was monitored, and the reactor was refilled to 100 psig when the pressure reached 50 psig. Samples of the reaction mixture were obtained at 30, 60, 90, and 120 minutes. The reaction was monitored using GC for both the disappearance of C18:2 olefins and the formation of C18:0 and C18:1 olefins. The reaction proceeded to 51.3% conversion with 97.3% selectivity to the C18:1 in 30 min. The reaction was gravity filtered and the clear product recovered.

Example 19

Selective Hydrogenation of C13 FAMEs with PRICAT 9908

In a 600 mL Parr reactor, 300 g of C13 FAMEs (94% C13) and 0.7442 g Pricat 9908 (0.25 wt %, triglycerides removed before reaction), was purged with $N_2$, then $H_2$ for 15 min each, then reacted at 150° C., 100 psig $H_2$, and 1000 rpm stirring with a gas dispersion impeller. The $H_2$ pressure was monitored and the reactor was refilled to 100 psig when it decreased to 50 psig. Samples of the reaction mixture were taken at 30 min, 1 h, 2 h, 3 h, and 4 h, and the reaction was monitored by GC for the disappearance of C13:2 FAMEs as well as the formation of C13:1 and 13:0 FAMEs. The reaction went to >99% completion with 96% selectivity towards C13:1 in 3 hours. The reaction mixture was gravity filtered and the clear product was recovered.

Example 20

Selective Hydrogenation of C13 FAMEs with PRICAT CU 50/8 P

In a 600 mL Parr reactor, 300 g of C13 FAMEs (94% C13) and 3.009 g Pricat Cu 50/8 P (1.0 wt %) was purged with $N_2$, then $H_2$ for 15 min each then reacted at 170° C., 300 psig $H_2$, and 1000 rpm stirring with a gas dispersion impeller. The $H_2$ pressure was monitored and the reactor was refilled to 100 psig when it decreased to 50 psig. Samples of the reaction mixture were taken at 30 min, 1 h, 2 h, 3 h, 4 h, and 5 h and the reaction was monitored by GC for the disappearance of C13:2 FAMEs as well as the formation of C13:1 and 13:0 FAMEs. The reaction went to >38% completion with 98% selectivity towards C13:1 in 5 hours. The reaction mixture was gravity filtered and the blue/green clear product was recovered. The product contains ca. 300 ppm Cu which leached off the catalyst.

Example 21

Purification of C13 FAME Feed by Alumina Column

The C13 FAME feedstock was analyzed by PV and Karl Fisher titration to have a PV of 37.25 meq/kg and a $H_2O$ content of 330 ppm. To purify the sample, the feedstock was passed through an activated alumina column, and then dried over 4 A molecular sieves overnight under a $N_2$ atmosphere. The PV was reduced to 2.17 meq/mg and the water reduced to 118 ppm.

Example 22

Selective Hydrogenation of C15 FAMEs with PRICAT 9908

In a 600 mL Parr reactor, 300 g C15 Feedstock (purified by alumina column and molecular sieves, >94% C15, 34.7% C15:2) and 0.30 g Pricat 9908 (0.1 wt %, triglycerides removed before reaction) was purged with $N_2$, then $H_2$ for 15 min each, then reacted at 150° C., 100 psig $H_2$, and 1000 rpm stirring with a gas dispersion impeller. The $H_2$ pressure was monitored and the reactor was refilled to 100 psig when it decreased to 50 psig. Samples of the reaction mixture were taken at 30 min, 1 h, 2 h, 3 h, and 4 h, and the reaction was monitored by GC for the disappearance of C15:2 FAMEs as well as the formation of C15:1 and 15:0 FAMEs. The reaction went to >87% completion with 81% selectivity towards C13:1 in 3 hours. The reaction mixture was gravity filtered and the clear product was recovered.

Example 23

Selective Hydrogenation of C13-15 FAMEs with PRICAT 9908

In a 600 mL Parr reactor, 300.46 g of C13 FAMEs (15% C13, 21% C14, 64% C15) and 0.2980 g Pricat 9908 (0.10 wt %, triglycerides removed before reaction), was purged with $N_2$, then $H_2$ for 15 min each, then reacted at 150° C., 100 psig $H_2$, and 1000 rpm stirring with a gas dispersion impeller. The $H_2$ pressure was monitored and the reactor was refilled to 100 psig when it decreased to 50 psig. Samples of the reaction mixture were taken at 30, 60, 90, and 120 min and the reaction was monitored by GC for the disappearance of polyunsaturated esters as well as the formation of monounsaturated esters and unsaturated esters. The reaction went to 88.5 completion with 95% selectivity towards monounsaturated esters in 3 hours. The reaction mixture was gravity filtered and the clear product was recovered.

Example 24

Diene-Selective Hydrogenation of Metathesized Soybean Oil with PRICAT 9908

In a 600 mL Parr reactor, 325.4 g MSBO and 0.6541 g Pricat 9908 (0.2 wt %, triglycerides removed before reaction), were purged with $N_2$, then $H_2$, for 15 min each, then reacted at 150° C., 100 psig $H_2$, and 1000 rpm stirring with a gas dispersion impeller. The $H_2$ pressure was monitored and the reactor was refilled to 100 psig when it decreased to 50 psig. Samples of the reaction mixture were taken at 15, 30, 45, 60, and 75 min. The samples were transesterified with methanol, and the reaction monitored by GC for the disappearance of C18:2 esters as well as the formation of C18:1 esters. The reaction mixture was vacuum filtered, and the product (DSHMSBO) was recovered.

Example 25

Oxidative Stability Study of Metathesized Soybean Oil (MSBO) and Diene-Selectively Hydrogenated Metathesized Soybean Oil (DSHMSBO)

To a series of 20 mL scintillation vials was added 18.0 g of either MSBO of PHMSBO. One sample of each material was sparged with $N_2$ for 5 min, then stored in a closed vial under a $N_2$ atmosphere. One sample of each material was stored in a closed vial under an atmosphere of air, and the final set of samples was stored in a vial open to the atmosphere. At 0, 11, 18, and 25 days the PV of the samples was tested in order to study the oxidative stability of the materials. After 25 days, the MSBO sample left open to air had a PV of 46.2 meq/kg, while the equivalent sample of DSHMSBO had a PV of 2.2 meq/kg.

A brief summary of the observations from the Examples above is provided in Tables 1 and 2 below.

TABLE 1

| Ex. | Summary/Observations |
|---|---|
| 1 | Diene-selective hydrogenation of C9/C10 olefins using PRICAT CU 50/8 P. Catalyst is selective toward monoene formation, but the reaction is slow. |

TABLE 1-continued

| Ex. | Summary/Observations |
|---|---|
| 2 | Diene-selective hydrogenation of C9/C10 olefins using PRICAT 9908. Catalyst is selective toward monoene formation, and the reaction is faster. |
| 3 | Diene-selective hydrogenation of C12 olefins using PRICAT 9908. The reaction is both fast and selective. |
| 4 | Diene-selective hydrogenation of C12 olefins using PRICAT 9908 and PRICAT CU 50/8 P. The PRICAT CU 50/8 P was used at 5% catalyst loading - this experiment demonstrated maintained selectivity despite contamination of the catalyst. |
| 5 | Diene-selective hydrogenation of C12 olefins using PRICAT CU 50/8 P and PRICAT 9908. The PRICAT 9908 was used at 5% catalyst loading - this experiment demonstrated maintained selectivity despite contamination of the catalyst. |
| 6 | Diene-selective hydrogenation of C12 olefins using PRICAT CU 50/8 P. The reaction is slightly slower; it is selective. |
| 7 | Diene-selective hydrogenation of C12 olefins using PRICAT CU 60/35 P. The reaction is slower to near full conversion. Selectivity appears to be maintained. |
| 8 | Purification of C12/C13 olefins by alumina column. Pre-treatment of feed using alumina showed significant increase in selectivity and speed of reaction. |
| 9 | Diene-selective hydrogenation of C12/C13 olefins using PRICAT 9908. This was selective, yet slow. |
| 10 | Diene-selective hydrogenation of C12/C13 olefins using PRICAT CU 50/8 P. This was a fast and selective reaction. |
| 11 | Diene-selective hydrogenation of C12/C13 olefins using recycled PRICAT CU 50/8 P. The reaction is as selective as that using the new catalyst, but it is a slower reaction. |
| 12 | Diene-selective hydrogenation of C12/C13 olefins using twice recycled PRICAT CU 50/8 P. The reaction maintains its selectivity, but slower than the reaction using the once recycled catalyst. |
| 13 | Diene-selective hydrogenation of unpurified C13 olefins. This reaction is prior to the use of alumina as pre-treatment; the selectivity obtained is high, but the conversion of the diene is extremely low. |
| 14 | Diene-selective hydrogenation of purified C13 olefins with PRICAT CU 50/8 P. Much higher conversion was obtained using the purification pre-treatment. |
| 15 | Diene-selective hydrogenation of purified C13 olefins with PRICAT 9908. The selectivity and speed of the reaction are both improved from the C13 olefins with the Pricat Cu 50/8P catalyst. |
| 16 | Diene-selective hydrogenation of C15-18 olefins using PRICAT CU 50/8 P. Despite a slow reaction, the selectivity was high. |
| 17 | Diene-selective hydrogenation of C18 olefins with PRICAT CU 50/8 P. This was a faster reaction with high selectivity. |
| 18 | Diene-selective hydrogenation of C18 olefins with PRICAT 9908. The reaction showed low conversion, but high selectivity. |
| 19 | Diene-selective hydrogenation of C13 FAMEs with PRICAT 9908. The reaction was selective towards monounsaturated ester, and is fast for an ester. |
| 20 | Diene-selective hydrogenation of C13 FAMEs with PRICAT 50/8 P. The reaction was selective towards monounsaturated ester, but is much slower than with the PRICAT 9908. |
| 21 | Purification of C13 FAMEs by alumina column. Pre-treatment of feed using alumina showed significant increase in selectivity and speed of reaction. |
| 22 | Diene-selective hydrogenation of purified C15 FAMEs with PRICAT 9908. The reaction was selective towards mono-olefin ester, but is slower than the C13 FAMEs with the same catalyst. |
| 23 | Diene-Selective hydrogenation of C13-15 FAMEs with PRICAT 9908. The reaction was selective to mono-olefin esters and was fast. |
| 24 | Diene-Selective hydrogenation of metathesized soybean oil with PRICAT 9908. The reaction was selective to mono-unsaturated esters. |
| 25 | Oxadative stability study of metathesized soybean oil (MSBO) and diene-selectively hydrogenated metathesized soybean oil (DSHMSBO) by peroxide value. The PV of MSBO is ~20x that of DSHMSBO after storage for 25 days in air. |

TABLE 2

| Ex. | Feedstock (g) | Treated Feedstock | Catalyst loading (g) | Reaction time (min) | Conversion (%)[1] | Selectivity (%)[2] |
|---|---|---|---|---|---|---|
| 1 | 300 | N | 1.52 | 30 | 95 | 92 |
| 2 | 300 | N | 0.74 | 120 | 85 | 95 |
| 3 | 300 | Y | 0.31 | 30 | 96.5 | 98.4 |
| 4 | 300 | Y | 0.32 | 30 | 94.3 | 97.6 |
| 5 | 300 | Y | 0.95 | 30 | 96.7 | 92.9 |
| 6 | 300 | Y | 0.90 | 30 | 98.6 | 99.7 |
| 7 | 300 | Y | 0.90 | 90 | 73.3 | 99.4 |
| 9 | 300 | Y | 0.30 | 90 | 78.3 | 94.0 |
| 10 | 300 | Y | 0.90 | 30 | 97.7 | 97.2 |
| 11 | 300 | Y | 1.33[3] | 60 | 93.2 | 98.2 |
| 12 | 300 | Y | 1.05[4] | 60 | 94.4 | 99.5 |
| 13 | 300 | N | 3.10 | 120 | 27.3 | 99.6 |
| 14 | 300 | Y | 3.04 | 120 | 96.8 | 91.9 |
| 15 | 300 | Y | 0.29 | 60 | 98.6 | 94.9 |
| 16 | 300 | Y | 0.30 | 90 | 86.7 | 99.5 |
| 17 | 300 | Y | 0.31 | 45 | 93.8 | 99.4 |
| 18 | 300 | Y | 0.07 | 30 | 51.3 | 97.3 |
| 19 | 300 | N | 0.74 | 180 | 99 | 96 |
| 20 | 300 | N | 3.01 | 300 | 38 | 98 |
| 22 | 300 | Y | 0.30 | 180 | 87 | 81 |

TABLE 2-continued

| Ex. | Feedstock (g) | Treated Feedstock | Catalyst loading (g) | Reaction time (min) | Conversion (%)[1] | Selectivity (%)[2] |
|---|---|---|---|---|---|---|
| 23 | 300 | N | 0.30 | 180 | 88.5 | 95 |
| 24 | 325 | N | 0.65 | 75 | 67.5[5] | 93.3 |

[1] Conversion is defined as (total polyunsaturates in feed − total polyunsaturates in product/ total polyunsaturates in feed)
[2] Selectivity is defined as (total monounsaturates in product/total monounsaturates in product + total saturates in product)
[3] Catalyst was recycled once before use
[4] Catalyst was recycled twice before use
[5] Conversion for DSHMSBO was determined as C18:2 conversion to C18:1 and C18:0

Unless otherwise described, the following analytical methods described below were used when analyzing the ester compositions in the aforementioned examples:

Volatile products were analyzed by gas chromatography and flame ionization detector (FID). Fatty acid methyl ester (FAME) analyses were performed using an Agilent 6890 instrument and conditions including, but not limited to, the following methods:

Method 1: Column: Restek Rtx-wax, carbowax 12438-6850, 30 m×250 um×0.50 um film thickness
Injector temperature: 250° C.
Detector temperature: 300° C.
Oven temperature: 100° C. starting temperature, 2 minute hold time, ramp rate 5° C./min to 240° C., 35 minute run time
Carrier gas: Hydrogen
Mean gas velocity: 33 cm/sec
Split ratio: 150:1
Method 2: Column: Restek Rtx-wax, carbowax 12438-6850, 30 m×250 um×0.50 um film thickness
Injector temperature: 250° C.
Detector temperature: 300° C.
Oven temperature: 70° C. starting temperature, 1 minute hold time, ramp rate 20° C./min to 180° C., ramp rate 1.5° C./min to 240° C., 3.5 minute hold time, 50 minute runtime
Carrier gas: Hydrogen
Mean gas velocity: 54 cm/sec
Split ratio: 150:1
Method 3: Column: Restek Rtx-wax, carbowax 12438-6850, 30 m×250 um×0.50 um film thickness
Injector temperature: 250° C.
Detector temperature: 300° C.
Oven temperature: 70° C. starting temperature, 1 minute hold time, ramp rate 20° C./min to 180° C., 0 minute hold time, ramp rate 3° C./min to 240° C., 3.5 minute hold time, 30 minute run time
Carrier gas: Hydrogen
Mean gas velocity: 54 cm/sec
Split ratio: 150:1

Unless otherwise described, the following analytical methods described below were used when analyzing the olefin compositions in the aforementioned examples:

Volatile products were analyzed by gas chromatography and flame ionization detector (FID). Olefin analyses were performed using an Agilent 6890 instrument and conditions including, but not limited to, the following methods:

Method 1: Column: Restek Rtx-wax, carbowax 12438-6850, 30 m×250 um×0.50 um film thickness
Injector temperature: 250° C.
Detector temperature: 300° C.
Oven temperature: 40° C. starting temperature, 5 minute hold time, ramp rate 10° C./min to 240° C., 25 minute run time
Carrier gas: Hydrogen
Mean gas velocity: 29 cm/sec
Split ratio: 150:1
Method 2: Column: Restek Rtx-wax, carbowax 12438-6850, 30 m×250 um×0.50 um film thickness
Injector temperature: 250° C.
Detector temperature: 300° C.
Oven temperature: 70° C. starting temperature, 5 minute hold time, ramp rate 5° C./min to 240° C., 5 minute hold time, 44 minute run time
Carrier gas: Hydrogen
Mean gas velocity: 31 cm/sec
Split ratio: 150:1

The products were characterized by comparing peaks with known standards, in conjunction with supporting data from mass spectrum analysis (GCMS-Agilent 5973N).
Column: Crossbond 65% diphenyl, 30 m×250 um×0.1 um
Injector temperature: 275° C.
Detector temperature: 375° C.
Oven temperature: 40° C. starting temperature, 5 minute hold time, ramp rate 20° C./min to 350° C., 31.5 minute hold time, 60 minute run time
Carrier gas: Helium
Average velocity: 51.282 cm/sec
Split ratio: 20:1

The examples above collectively demonstrate the major steps described in the process schemes, showing the production of olefins, paraffins, metathesized triglycerides, unsaturated fatty acid esters and acids, and diacid compounds from natural oils that are useful as chemicals, solvents and fuels blending stocks.

What is claimed is:

1. A method of refining a natural oil, comprising:
providing a feedstock comprising a natural oil;
reacting the feedstock in a metathesis reactor in the presence of a metathesis catalyst to form a metathesized product comprising polyunsaturated olefins and polyunsaturated esters; and
partially hydrogenating the polyunsaturated olefins and/or the polyunsaturated esters in the presence of a hydrogenation catalyst, wherein at least a portion of the polyunsaturated olefins and/or polyunsaturated esters are converted into monounsaturated olefins and/or monounsaturated esters.

2. The method of claim 1, further comprising separating the polyunsaturated olefins in the metathesized product from the polyunsaturated esters in the metathesized product prior to the hydrogenating step.

3. The method of claim 2, wherein at least a portion of the polyunsaturated olefins are converted into the monounsaturated olefins.

4. The method of claim 3, wherein the hydrogenating step has a conversion rate of at least 85% and a selectivity of at least 90%.

5. The method of claim 3, wherein the hydrogenating step has a conversion rate of at least 90% and a selectivity of at least 95%.

6. The method of claim 3, wherein the hydrogenating step has a conversion rate of at least 95% and a selectivity of at least 99%.

7. The method of claim 2, following the separating step and prior to the hydrogenating step, transesterifying the polyunsaturated esters in the presence of an alcohol to form a transesterified product.

8. The method of claim 2, following the separating step and the hydrogenating step, transesterifying the monounsaturated esters in the presence of an alcohol to form a transesterified product.

9. The method of claim 2, wherein at least a portion of the polyunsaturated olefins are converted into the monounsaturated esters.

10. The method of claim 9, wherein the hydrogenating step has a conversion rate of at least 85% and a selectivity of at least 90%.

11. The method of claim 9, wherein the hydrogenating step has a conversion rate of at least 90% and a selectivity of at least 95%.

12. The method of claim 9, wherein the hydrogenating step has a conversion rate of at least 95% and a selectivity of at least 99%.

13. The method of claim 2, wherein at least a portion of the polyunsaturated olefins are converted to the monounsaturated olefins and at least a portion of the polyunsaturated esters are converted to monounsaturated esters.

14. The method of claim 1, wherein the hydrogenation catalyst comprises a metal selected from the group consisting of nickel, copper, palladium, platinum, molybdenum, iron, ruthenium, osmium, rhodium, iridium, and combinations thereof.

15. The method of claim 1, wherein the hydrogenation catalyst is provided in an amount between 0.01-1.0 wt % of the polyunsaturated olefins and/or polyunsaturated esters.

16. The method of claim 1, wherein the hydrogenating step is conducted for 30-180 minutes at a temperature between 150° C. and 250° C. with a hydrogen gas pressure between 50 psig and 500 psig.

17. The method of claim 1, wherein the hydrogenation catalyst has been recycled prior to the hydrogenating step.

18. The method of claim 1, further comprising treating the feedstock, prior to reacting the feedstock in the presence of a metathesis catalyst, under conditions sufficient to diminish catalyst poisons in the feedstock, wherein the feedstock is treated with one or more of the following: heat, molecular sieves, alumina, silica gel, montmorillonite clay, fuller's earth, bleaching clay, diatomaceous earth, zeolites, kaolin, activated metals, acid anhydrides, activated carbon, soda ash, metal hydrides, metal sulfates, metal halides, metal carbonates, metal silicates, phosphorous pentoxide, metal aluminum hydrides, alkyl aluminum hydrides, metal borohydrides, organometallic reagents, and palladium on carbon catalysts.

19. The method of claim 18, wherein the feedstock is chemically treated through a chemical reaction to diminish the catalyst poisons, wherein the chemical reaction involves treating the feedstock with one or more of the following: metal hydrides, metal sulfates, metal halides, metal carbonates, metal silicates, phosphorous pentoxide, metal aluminum hydrides, alkyl aluminum hydrides, metal borohydrides, and organometallic reagents.

20. The method of claim 18, wherein the feedstock is heated to a temperature greater than 100° C. in the absence of oxygen and held at the temperature for a time sufficient to diminish the catalyst poisons.

21. The method of claim 1, further comprising providing a low-molecular-weight olefin or a mid-weight olefin, wherein the reacting step comprises a cross-metathesis reaction between the feedstock with the low-molecular-weight olefin or mid-weight olefin.

* * * * *